US006683175B2

(12) United States Patent
Tanaka

(10) Patent No.: US 6,683,175 B2
(45) Date of Patent: Jan. 27, 2004

(54) PORPHYRIN COMPOUND, AND ELECTROPHOTOGRAPHIC PHOTOSENSITIVE MEMBER, PROCESS-CARTRIDGE AND APPARATUS USING THE COMPOUND

(75) Inventor: Masato Tanaka, Suntoh-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 17 days.

(21) Appl. No.: 10/119,003

(22) Filed: Apr. 10, 2002

(65) Prior Publication Data

US 2002/0192581 A1 Dec. 19, 2002

(30) Foreign Application Priority Data

Apr. 12, 2001 (JP) ....................................... 2001-114345

(51) Int. Cl.$^7$ ......................... C07D 487/22; G03G 5/06
(52) U.S. Cl. ......................... 540/145; 430/78; 430/59.1
(58) Field of Search ................. 430/78, 59.1; 540/145; 399/159

(56) References Cited

U.S. PATENT DOCUMENTS

| | | | | |
|---|---|---|---|---|
| 3,895,944 A | * | 7/1975 | Wiedemann et al. | 430/78 |
| 5,109,016 A | * | 4/1992 | Dixon et al. | 540/145 |
| 5,122,247 A | * | 6/1992 | Kokado et al. | 430/58.15 |
| 5,515,393 A | | 5/1996 | Okuyama et al. | 372/45 |
| 5,811,212 A | | 9/1998 | Tanaka | 430/58 |
| 5,821,021 A | * | 10/1998 | Kawahara | 430/78 |
| 6,190,811 B1 | * | 2/2001 | Tanaka et al. | 430/78 |
| 6,245,472 B1 | | 6/2001 | Tanaka | 430/78 |
| 6,248,490 B1 | | 6/2001 | Suzuki et al. | 430/69 |

FOREIGN PATENT DOCUMENTS

| | | | | |
|---|---|---|---|---|
| JP | 63-106662 | | 5/1988 | |
| JP | 05275771 A | * | 10/1993 | H01L/49/02 |
| JP | 5-313033 | | 11/1993 | |
| JP | 5-333575 | | 12/1993 | |
| JP | 06136278 A | * | 5/1994 | C09B/47/08 |
| JP | 6-334272 | | 12/1994 | |
| JP | 7-321409 | | 12/1995 | |
| JP | 7-335975 | | 12/1995 | |
| JP | 8-088441 | | 4/1996 | |
| JP | 9-189930 | | 7/1997 | |
| JP | 9-240051 | | 9/1997 | |
| JP | 9-275242 | | 10/1997 | |

OTHER PUBLICATIONS

Datta–Gupta, N. et al. "Some metal complexes of a,b,g, d–tetra(4–pyridyl)porphine". Journal of Coordination Chemistry (1976), 5(4), 201–7.*

Fleischer, Everly B. "a,b,g,d,–Tetra–4–pyridylporphine and some of its metal complexes". Inorganic Chemistry (1962), 1, 493–5.*

Derwent Acc. No. 1994–197323 (1999).*

Borsenberger, Paul M. et al. Organic Photoreceptors for Imaging Systems. New York: Marcel–Dekker, Inc. (1993) pp. 6–17 & 289–292.*

Alder, et al.; "On the Preparation of Metalloporphyrins"; J. Inorg. Nucl. Chem., 1970, vol. 32, pp. 2643–2445.

Fischer, et al.; "Synthese des Porphins"; Ann. Chem. 521, 157 (1936).

* cited by examiner

*Primary Examiner*—Christopher Rodee
(74) *Attorney, Agent, or Firm*—Fitzpatrick, Cella, Harper & Scinto

(57) ABSTRACT

An electrophotographic photosensitive member having a sensitivity to a short semiconductor laser light in a wavelength range of 380–500 nm is provided by incorporating a specific porphyrin compound in a photosensitive layer. The porphyrin compound is characterized by having a heterocyclic substituent, preferably 4 heterocyclic substituents each of a pyridyl group. The porphyrin compound includes a 5,10,15,20-tetrapyridyl-21H,23H-porphyrinato-zinc compound having a novel crystal form characterized by certain peaks in a $CuK_{\alpha}$-characteristic X-ray diffraction pattern.

4 Claims, 15 Drawing Sheets

PORPHYRIN COMPOUND, AND ELECTROPHOTOGRAPHIC PHOTOSENSITIVE MEMBER, PROCESS-CARTRIDGE AND APPARATUS USING THE COMPOUND

FIELD OF THE INVENTION AND RELATED ART

The present invention relates to a porphyrin compound inclusive of a porphyrinato-zinc compound having a novel crystal form, an electrophotographic photosensitive member using such a porphyrin compound, and a process-cartridge and an electrophotographic apparatus including the photosensitive member.

Lasers currently used as exposure light sources in electrophotographic apparatus are predominantly semiconductor lasers having an oscillating wavelength around 800 nm or 680 nm.

In recent years, various approaches for realizing higher resolutions have been made so as to comply with increasing demands for output images of a higher image quality. The laser wavelengths are also concerned with realizing of the high resolution, and a shorter laser oscillation wavelength allows a smaller laser spot diameter facilitating a higher resolution electrostatic latent image formation.

Various proposals have been made for realizing shorter laser oscillation wavelengths.

One of such proposal is to reduce a laser light wavelength into a half by utilizing second harmonic generation (SHG) (JP-A 9-275242, JP-A 9-189930 and JP-A 5-313033). According to these proposals, GaAs laser and YAG laser already technically established and capable of high output power can be used as primary light sources, thus being able to realize a longer life or a larger output power.

Another proposal is to use wide-gap semiconductors, which allow a smaller size of device compared with the devices utilizing second harmonic generation. Lasers using ZnSe semiconductor (JP-A 7-321409 and JP-A 6-334272) and GaN semiconductor (JP-A 8-88441 and JP-A 7-335975) have been studied frequently in view of their high luminescence efficiency.

Such a semiconductor laser has posed difficulties in optimization of device structure, crystal growth conditions, electrodes, etc., and a long term oscillation at room temperature which is essential for commercialization has been obstructed due to occurrence of crystal defects, etc.

However, along with a technical innovation of substrates, etc., a report has been made on continuous oscillation for 1150 hours of a GaN semiconductor laser (at 50° C.) in October 1997 from Nichia Kagaku Kogyo K.K., and a commercialization thereof is near at hand.

On the other hand, in electrophotographic photosensitive members used in conventional laser-equipped electrophotographic apparatus, charge-generating materials having a large absorption band and showing a practical sensitivity characteristic around 700–800 nm have been used, inclusive of non-metallic phthalocyanine, copper phthalocyanine and oxytitanium phthalocyanine, as specific examples.

However, such a charge-generating substance for long-wavelength lasers does not have a sufficient absorption band around 400–500 nm or, if any, is encountered with a difficulty in stably exhibiting a sufficient sensitivity due to a strong wavelength-dependence.

JP-A 9-240051 has disclosed an electrophotographic photosensitive member having a single layer-type photosensitive layer or a laminate-type photosensitive layer including a charge generation layer using a charge-generating material comprising an α-form oxytitanium phthalocyanine as an electrophotographic photosensitive member suitable for a laser of 400–500 nm. According to our study, however, the use of the charge-generating material is accompanied with not only a low sensitivity but also a problem of resulting in an electrophotographic photosensitive member showing a large potential fluctuation in repetitive use due to a very large memory characteristic for light around 400 nm.

As for porphyrin compounds, JP-A 63-106662 has disclosed an electrophotographic photosensitive member using a 5,10,15,20-tetraphenyl-21H,23H-porphyrin compound in its charge generation layer, but has not succeeded in providing a commercial level of sensitivity characteristic.

Further, JP-A 5-333575 mentions tetrapyridyl-porphyrin as an example of an N-type conductive pigment to be used in combination with a phthalocyanine compound for providing a charge-generating material but contains no specific further description about the tetrapyridyl porphyrin.

For reference, syntheses of porphyrin compounds have been reported in, e.g., 1) H. Fisher and W. Glein, ANN. Chem. 521,157 (1936); 2) R. Rothemund, J. Amer. Chem. Soc., 58,525 (1936); 3) A. Adler, F. Longo, F. Kampas and J. Kim., J. Inorg. Nucl. Chem. 32,2442 (1970); and 4) A. Shamin, P. Worthington and P. Hambright, J. Chem. Soc. Pak. 3(1), p. 1-3 (1981).

SUMMARY OF THE INVENTION

An object of the present invention is to provide a porphyrin compound suitable for use as a charge-generating material in an electrophotographic photosensitive member.

A more specific object of the present invention is to provide a tetrapyridyl-porphyrin compound, particularly a tetrapyridyl porphyrinato-zinc compound having a novel crystal form.

Another object of the present invention to provide an electrophotographic photosensitive member showing a high sensitivity in a wavelength region of 380–500 nm by using such a tetrapyridyl-porphyrin compound.

Further objects of the present invention are to provide a process-cartridge and an electro-photographic apparatus equipped with such an electrophotographic photosensitive member.

According to the present invention, there is provided a 5,10,15,20-tetrapyridyl-21H,23H-porphyrinato-zinc compound having a crystal form selected from the group consisting of (a), (b) and(c) shown below:

(a) a crystal form characterized by peaks at Bragg angles (2θ±0.2 deg.) of 9.4 deg., 14.2 deg. and 22.2 deg., (b) a crystal form characterized by peaks at Bragg angles (2θ±0.2 deg.) of 7.0 deg., 10.5 deg. and 22.4 deg., and (c) a crystal form characterized by peaks at Bragg angles (2θ±0.2 deg.) of 7.4 deg., 10.2 deg and 18.3 deg., respectively in $CuK_\alpha$-characteristic X-ray diffraction patterns.

According to another aspect of the present invention, there is provided an electrophotographic photosensitive member, comprising a support and a photosensitive layer disposed on the support, wherein the photosensitive layer contains a porphyrin compound having a structure represented by formula (1) shown below:

(1),

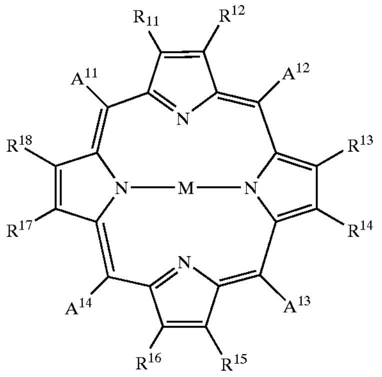

wherein M denotes a hydrogen atom or a metal capable of having an axial ligand; $R^{11}$ and $R^{18}$ independently denote a hydrogen atom, an alkyl group capable of having a substituent, an aromatic ring capable of having a substituent, an amino group capable of having a substituent, a sulfor atom capable of having a substituent, an alkoxy group, a halogen atom, a nitro group or a cyano group; and $A^{11}$ to $A^{14}$ independently denote a hydrogen atom, an alkyl group capable of having a substituent, an aromatic ring capable of having a substituent or a heterocyclic ring capable of having a substituent with the proviso that at least one of $A^{11}$ to $A^{14}$ is a heterocyclic group capable of having a substituent.

The present invention further provides a process-cartridge and an electrophotographic apparatus equipped with the above-mentioned electrophotographic photosensitive member.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
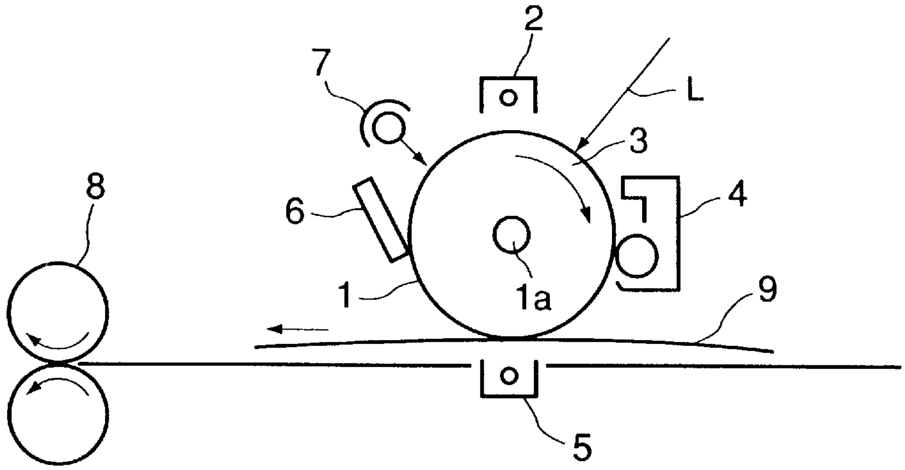
FIG. 1 is a schematic illustration of an electrophotographic apparatus equipped with a photosensitive member of the invention.

The porphyrin compound used in the electrophotographic photosensitive member of the present invention has a structure represented by formula (1) shown below:

(1)

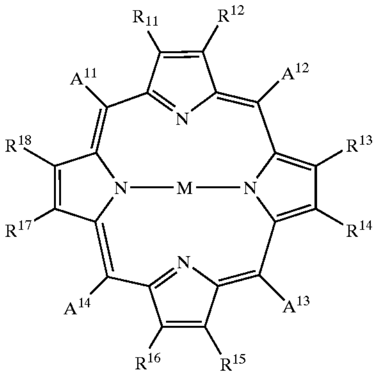

In the above formula, M denotes hydrogen atoms or a metal capable of having an axial ligand, i.e., a ligand coordinating to the melt M in a direction perpendicular to or intersecting with the porphyrin ring plane.

In the case where M is hydrogen atoms, the formula (1) is reduced to formula (1A) shown below:

(1A)

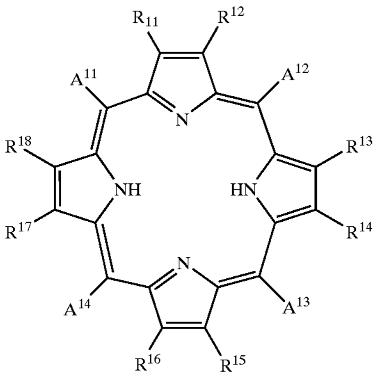

Examples of the metal M capable of having an axial ligand may include: Mg, Zn, Ni, Cu, V, Ti, Ga, Sn, In, Al, Mn, Fe, Co, Pb, Ge and Mo, and examples of the axial ligand may include: halogen atoms, oxygen atom, hydroxy group, alkoxy groups, amino group and alkylamino groups.

$R^{11}$ to $R^{18}$ independently denote a hydrogen atom, an alkyl group capable of having a substituent, an aromatic ring capable of having a substituent, an alkoxy group, a halogen atom, a nitro group or a cyano group.

Further, $A^{11}$ to $A^{14}$ independently denote a hydrogen atom, an alkyl group capable of having a substituent, an aromatic ring capable of having a substituent or a heterocyclic ring capable of having a substituent with the proviso that at least one of $A^{11}$ to $A^{14}$ is a heterocyclic group capable of having a substituent.

Examples of the alkyl group may include: methyl, ethyl, propyl and butyl. Examples the aromatic ring may include: benzene ring, naphthalene ring and anthracene ring. Examples of the alkoxy group may include: methoxy and ethoxy. Examples of the halogen atom may include: fluorine, chlorine, bromine and iodine. Examples of the heterocyclic ring may include: pyridine ring, thiophene ring, imidazole ring, pyrazine ring, triazine ring, indole ring, coumarin ring, fluorene ring, benzofuran ring, furan ring and pyran ring.

Examples of the optionally possessed substituent may include: alkyl groups, such as methyl, ethyl, propyl and butyl; alkoxy groups, such as methoxy and ethoxy; alkylamino groups, such as methylamino, dimethylamino and diethylamino; arylamino groups, such as phenylamino and diphenylamino; halogen atoms, such as fluorine, chlorine and bromine; hydroxy, nitro, cyano; and halomethyl groups, such as trifluoromethyl.

Among the porphyrin compounds represented by the above-mentioned formula (1), it is preferred to use a 5,10,15,20-tetrapyridyl-21H,23H-porphyrin compound corresponding to the case where each of $A^{11}$ and $A^{14}$ is a pyridyl group. It is particularly preferred to use a 5,10,15,20-tetra(4-pyridyl)-21H,23H-porphyrin compound obtained in the case where each pyridyl group is 4-pyridyl group.

Among the 5,10,15,20-tetrapyridyl-21H,23H-porphyrin compounds, it is preferred to use 5,10,15,20-tetrapyridyl-21H,23H-porphyrin compounds having a crystal form characterized by a $CuK_{\alpha}$-characteristic X-ray diffraction pattern showing a peak at a Bragg angle 2θ of 20.0±1.0 deg. inclusive of: 5,10,15,20-tetra(4-pyridyl)-21H,23H-porphyrin compound having a crystal form characterized by peaks at Bragg angles (2θ±0.2 deg.) of 8.2 deg., 19.7 deg., 20.8 deg., and 25.9 deg.; 5,10,15,20-tetra(3-pyridyl)-21H,23H-porphyrin compound having a crystal form characterized by peaks at Bragg angles (2θ±0.2 deg.) of 7.1 deg., 8.4 deg., 15.6 deg., 19.5 deg., 21.7 deg., 22.4 deg. and 23.8 deg.; and 5,10,15,20-tetra(2-pyridyl)-21H,23H-porphyrin compound having a crystal form characterized by a Bragg angle (2θ±0.2 deg.) of 20.4 deg, respectively in $CuK_{\alpha}$-characteristic X-ray diffraction patterns. Among the above, 5,10,15,20-tetra(4-pyridyl)-21H,23H-porphyrin compound having a crystal form characterized by peaks at Bragg angle (2θ±0.2 deg.) of 8.2 deg., 19.7 deg., 20.8 deg. and 25.9 deg. in a $CuK_{\alpha}$-characteristic X-ray diffraction pattern herein called (Crystal E), is particularly preferred.

Further, among the 5,10,15,20-tetra(4-pyridyl)-21H,23H-porphyrin compounds, a 5,10,15,20-tetra(4-pyridyl)-21H,23H-porphyrinato-zinc compound is preferred. It is particularly preferred to use a 5,10,15,20-tetra(4-pyridyl)-21H,23H-porphyrinato-zinc compound having a crystal form selected from:

(a) a crystal form characterized by peaks at Bragg angles (2θ±0.2 deg.) of 9.4 deg., 14.2 deg. and 22.2 deg. (herein called Crystal A), (b) a crystal form characterized by peaks at Bragg angles (2θ±0.2 deg.) of 7.0 deg., 10.5 deg. and 22.4 deg. (Crystal B), (c) a crystal form characterized by peaks at Bragg angles (2θ±0.2 deg.) of 7.4 deg., 10.2 deg and 18.3 deg. (Crystal C), and (d) a crystal form characterized by peaks at Bragg angles (2θ±0.2 deg.) of 9.1 deg., 10.6 deg., 11.2 deg. and 14.5 deg. (Crystal D) respectively in $CuK_{\alpha}$-characteristic X-ray diffraction patterns.

Hereinbelow, some examples of the porphyrin compound used in the electrophotographic photosensitive member of the present invention are enumerated with their structural formulae, but they are not exhaustive.

(1-1)

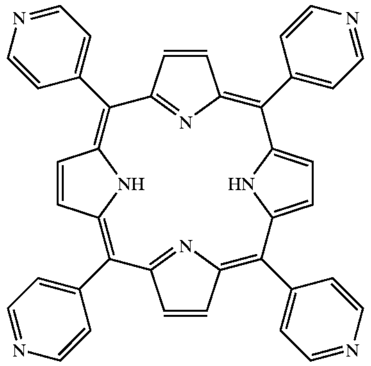

(1-2)

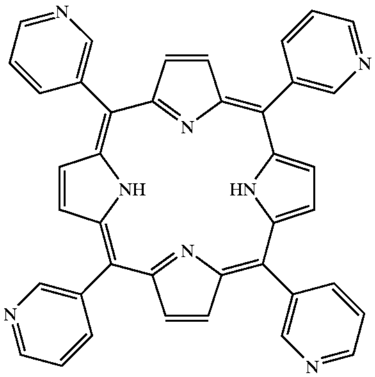

(1-3)

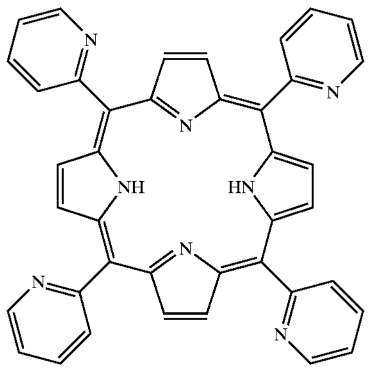

(1-4)

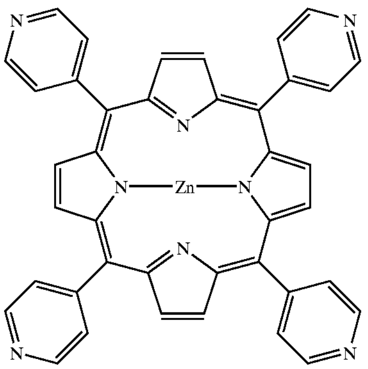

-continued
(1-5)
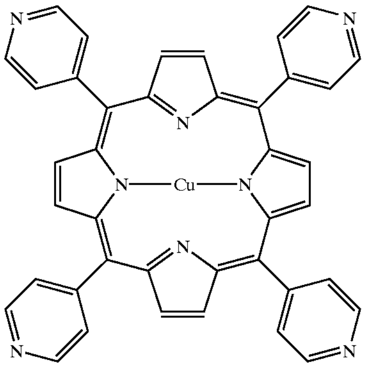
(1-6)
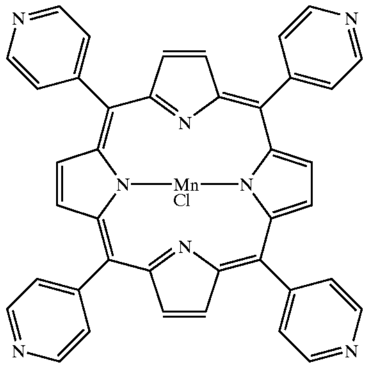
(1-7)
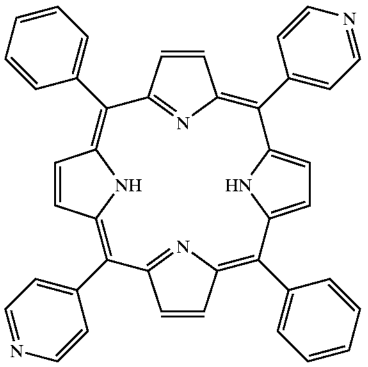
(1-8)
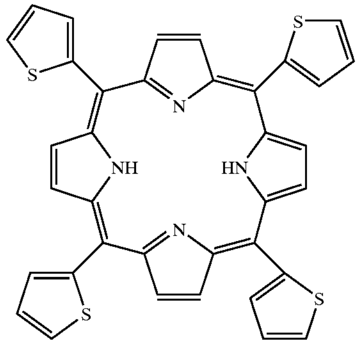
(1-9)
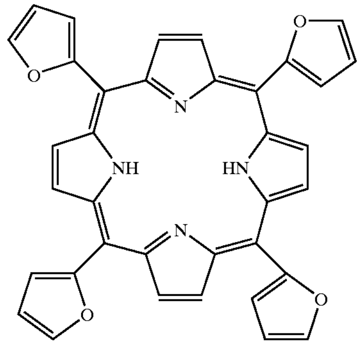
(1-10)
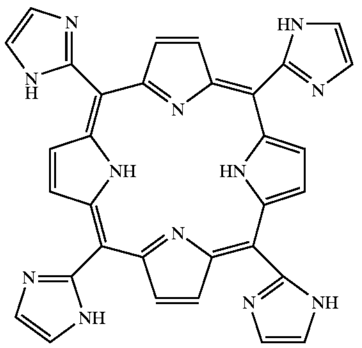
(1-11)
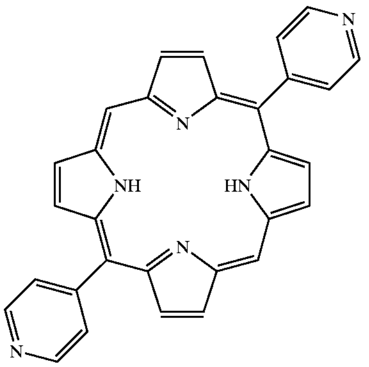
(1-12)
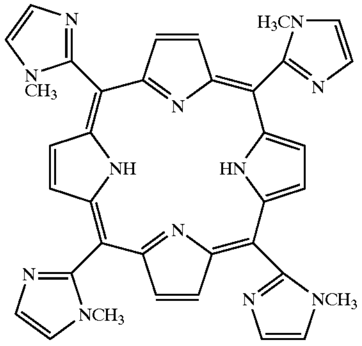

-continued

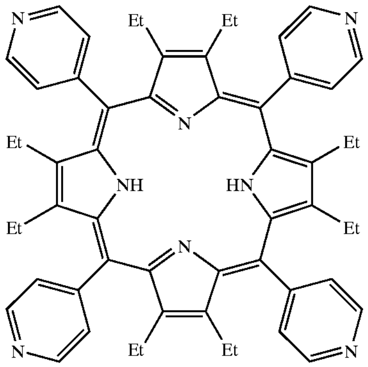

(1-13)

The 5,10,15,20-tetra(4-pyridyl)-21H,23H-porphyrinato-zinc compound having a crystal form characterized by peaks at Bragg angles (2θ±0.2 deg.) of 9.4 deg., 14.2 deg. and 22.2 deg. in a $CuK_\alpha$-characteristic X-ray pattern (Crystal A) may be formed by subjecting 5,10,15,20-tetra(4-pyridyl)-21H, 23H-porphyrinato-zinc compound obtained by reaction under heating of metal-free 5,10,15,20-tetra(4-pyridyl)-21H,23H-porphyrin compound with a zinc compound, such as zinc chloride, to conversion into an amorphous form by dry-milling together with glass beads in a sand mill, a paint shaker, etc., and then milling or stirring in the presence of a halide solvent, such as methylene chloride or chloroform.

The 5,10,15,20-tetra(4-pyridyl)-21H,23H-porphyrinato-zinc compound having a crystal form characterized by peaks at Bragg angles (2θ+0.2 deg.) of 7.0 deg., 10.5 deg., 17.8 deg. and 22.4 deg. in a $CuK_\alpha$-characteristic X-ray pattern (Crystal B) may be formed by subjecting 5,10,15,20-tetra (4-pyridyl)-21H,23H-porphyrinato-zinc compound obtained by reaction under heating of metal-free 5,10,15,20-tetra(4-pyridyl)-21H,23H-porphyrin compound with a zinc compound, such as zinc chloride, to conversion into an amorphous form by dry-milling together with glass beads in a sand mill, a paint shaker, etc., and then milling or stirring in the presence of an amide solvent such as N,N-dimethylformamide or N-methylpyrrolidone.

The 5,10,15,20-tetra(4-pyridyl)-21H,23H-porphyrinato-zinc compound having a crystal form characterized by peaks at Bragg angles (2θ±0.2 deg.) of 7.4 deg., 10.2 deg. and 18.3 deg. in a $CuK_\alpha$-characteristic X-ray pattern (Crystal C) may be formed by subjecting 5,10,15,20-tetra(4-pyridyl)-21H, 23H-porphyrinato-zinc compound obtained by reaction under heating of metal-free 5,10,15,20-tetra(4-pyridyl)-21H,23H-porphyrin compound with a zinc compound, such as zinc chloride, to conversion into an amorphous form by dry-milling together with glass beads in a sand mill, a paint shaker, etc., and then milling or stirring in the presence of an alcohol solvent, such as methanol, ethanol or propanol.

Herein, "milling" means a grinding treatment together with dispersion media, such as glass beads, steel beads or alumina beads, and "stirring" means a stirring without using such dispersion media.

Hereinbelow, the use of the porphyrin compound as a charge-generating material in the electrophotographic photosensitive member of the present invention will be described.

The electrophotographic photosensitive member according to the present invention may have a laminar structure including a single photosensitive layer containing both a charge-generating material and a charge-transporting material formed on an electroconductive support, or alternatively a laminar photosensitive layer including a charge generation layer containing a charge-generating material and a charge transport layer containing a charge-transporting material formed successively on a support. The order of lamination of the charge generation layer and the charge transport layer can be reversed.

The support may comprise any material exhibiting electroconductivity, examples of which may include: metals, such as aluminum and stainless steel. In addition, it is also possible to use a substrate of plastic (such as polyethylene, polypropylene, polyvinyl chloride, polyethylene terephthalate, acrylic resin or polyethylene fluoride) coated with a vacuum-deposited film of aluminum, aluminum alloy, indium oxide, tin oxide or indium tin oxide; a substrate of plastic or above-mentioned support material coated with a layer of electroconductive particles (of e.g., aluminum, titanium oxide, tin oxide, zinc oxide, carbon black or silver) together with an appropriate binder resin; a plastic or paper support impregnated with electroconductive particles; or a plastic support comprising an electroconductive polymer. The support may assume a form of a cylinder, or a flat, curved or wound sheet or belt. It is particularly suitable to use a cylindrical aluminum support in view of mechanical strength, electrophotographic performances and cost. A crude aluminum pipe may be used as it is, or after treatments inclusive of physical treatments, such as honing, and chemical treatments, such as anodic oxidation or acid treatment.

Between the support and the photosensitive layer, it is possible to dispose a primer layer or undercoating layer having a barrier function and an adhesive function. The undercoating layer may for example comprise a material, such as polyvinyl alcohol, polyethylene oxide, ethyl cellulose, methyl cellulose, casein, polyamide (such as nylon 6, nylon 66, nylon 610, copolymer nylon or N-alkoxymethylated nylon), polyurethane, glue, aluminum oxide or gelatin. These materials may be dissolved or dispersed in an appropriate solvent to be applied onto the support, thereby forming a film in a thickness of, preferably 0.1–μm, more preferably 0.5–5 μm.

The photosensitive layer of a single layer may be formed by mixing the porphyrin compound having a structure represented by the formula (1) as a charge-generating material and a charge-transporting material in an appropriate binder resin solution to form a mixture liquid and applying the mixture liquid onto the support, optionally via an undercoating layer as described above, followed by drying.

In the case of forming a laminar photosensitive layer as described above, the charge generation layer may suitably be formed by dispersing the porphyrin compound represented by the formula (1) in an appropriate binder solution to form a dispersion liquid and applying the dispersion liquid, followed by drying. However, the charge generating layer can also be formed by vapor deposition of the porphyrin compound.

The charge transport layer may be formed by applying and drying a paint formed by dissolving a charge-transporting material and a binder resin in a solvent. Examples of the charge-transporting material may include: triarylamine compounds, hydrazone compounds, stilbene compounds, pyrazoline compounds, oxazole compounds, thiazole compounds, and triarylmethane compounds.

Examples of the binder resin for constituting the above-mentioned photosensitive layer or constituent layers thereof may include: polyesters, acrylic resins, polyvinylcarbazole, phenoxy resins, polycarbonates, polyvinyl butyral, polystyrene, polyvinyl acetate, polysulfone, polyarylate, polyvinylidene chloride, acrylonitrile copolymer, and polyvinylbenzal.

The application of the photosensitive layer(s) may be performed by coating methods, such as dipping, spray coating, spinner coating, bead coating, blade coating and beam coating.

The single-layered photosensitive layer may have a thickness of 5–40 μm, preferably 10–30 μm. In the laminar photosensitive layer, the charge generation layer may have a thickness of 0.01–10 μm, preferably 0.05–5 μm, and the charge transport layer may have a thickness of 5–30 μm, preferably 10–30 μm. The charge-generating material may preferably be contained in 20–90 wt. %, more preferably 50–80 wt. %, of the charge generation layer. The charge-transporting material may preferably be contained in 20–80 wt. %, more preferably 30–70 wt. %, of the charge transport layer.

The single-layered photosensitive layer may preferably contain 3–30 wt. % of the charge-generating material and 30–70 wt. % of the charge-transporting material, respectively with respect to the total weight thereof.

The porphyrin compound of the formula (1) can be used in mixture with another charge-generating material if such is desired. In such cases, the porphyrin compound may preferably constitute at least 50 wt. % of the total charge-generating materials.

The photosensitive layer may be further coated with a protective layer as desired. Such a protective layer may be formed by applying a solution in an appropriate solvent of a resin, such as polyvinyl butyral, polyester, polycarbonate resin (such as polycarbonate Z or modified polycarbonate), polyamide, polyimide, polyarylate, polyurethane, styrene-butadiene copolymer, styrene-acrylic acid copolymer or styrene-acrylonitrile copolymer onto a photosensitive layer, followed by drying. The protective layer may preferably be formed in a thickness of 0.05–20 μm. The protective layer can contain electroconductive particles, an ultraviolet absorber or/and an anti-wearing agent. The electroconductive particles may for example comprise particles of a metal oxide, such as tin oxide. The anti-wearing agent may for example comprise a fluorine-containing resin, alumina or silica.

Next, some embodiments of structure and operation of the electrophotographic apparatus including an electrophotographic photosensitive member according to the present invention will be described.

Referring to FIG. 1, a drum-shaped photosensitive member 1 according to the present invention is driven in rotation at a prescribed peripheral speed in an indicated arrow direction about a shaft 1*a*. During the rotation, the outer peripheral surface of the photosensitive member 1 is uniformly charged by charging means 2 at a prescribed positive or negative potential, and then exposed to light-image L (as by slit exposure or laser beam scanning exposure) by using an imagewise exposure means (not shown), whereby an electrostatic latent image corresponding to an exposure image is successively formed on the peripheral surface of the photosensitive member 1. The electrostatic latent image is then developed with a toner by developing means 4 to form a toner image on the photosensitive member 1. The toner image is transferred by corona transfer means 5 onto a recording material 9 which has been supplied from a paper supply unit (not shown) to a position between the photosensitive member 1 and the transfer means 5 in synchronism with the rotation of the photosensitive member 1. The recording material 9 carrying the received toner image is then separated from the photosensitive member surface and guided to an image fixing device 8 to fix the toner image. The resultant print or copy comprising the fixed toner image is then discharged out of the electrophotographic apparatus. The surface of the photosensitive member 1 after the image transfer is subjected to removal of the residual toner by a cleaning means 6 to be cleaned and then subjected to charge removal by a pre-exposure means 7, to be recycled for repetitive image formation.

Figure 2:
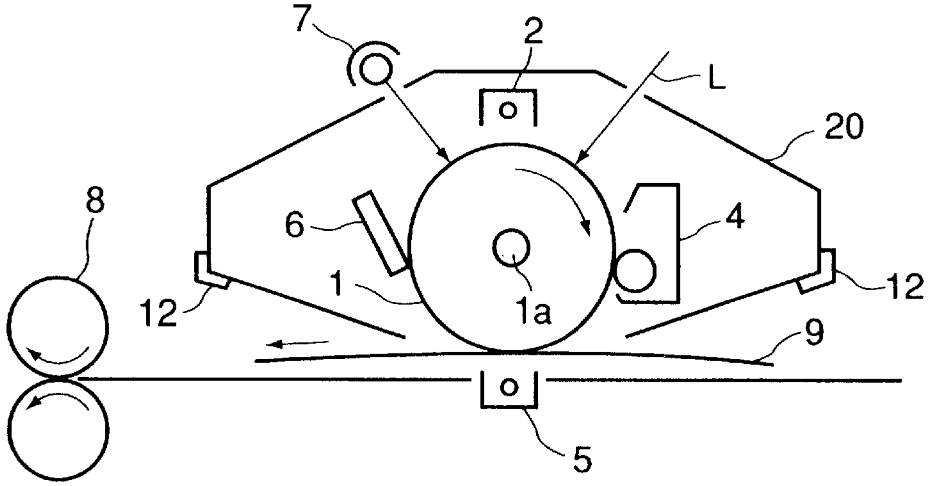
FIGS. 2 and 3 are respectively a schematic illustration of an electrophotographic apparatus equipped with a process-cartridge including a photosensitive member of the invention.

FIG. 2 shows another embodiment of the electrophotographic apparatus wherein at least a photosensitive member 1, a charging means 2 and a developing means 4 are housed within a container 20 to form a process cartridge, which is detachably mountable or insertable to a main assembly of the electrophotographic apparatus along a guide means 12, such as a guide rail, provided to the main assembly. A cleaning means 6 disposed within the container 20 in this embodiment can be omitted or disposed outside the container 20.

Figure 3:
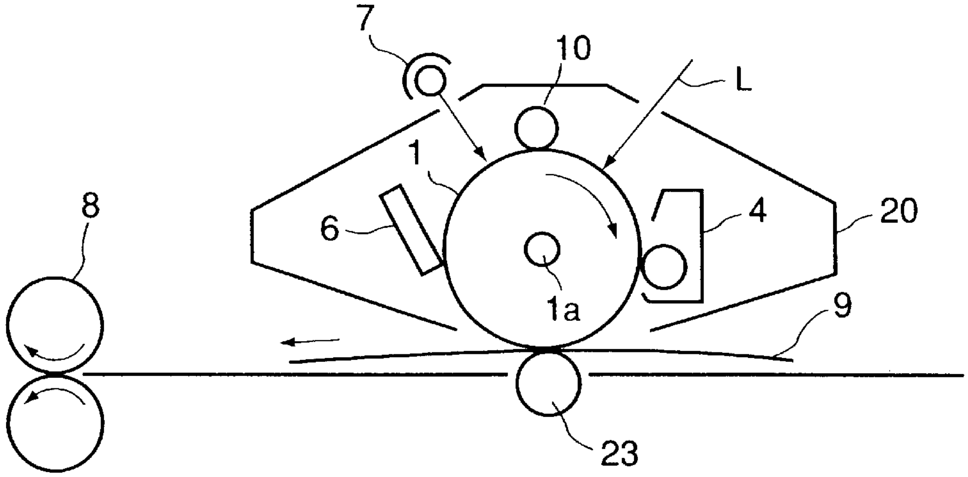
Figure 4:
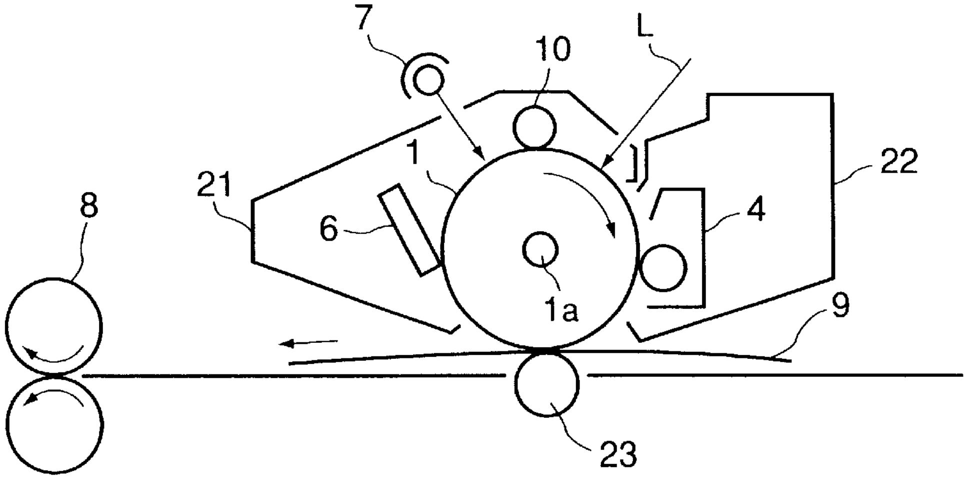
FIG. 4 is a schematic illustration of an electrophotographic apparatus equipped with a first process-cartridge including a photosensitive member of the invention, and also a second process-cartridge.

On the other hand, as shown in FIGS. 3 and 4, it is possible to use a contact charging member 10 and cause the contact charging member 10 supplied with a voltage to contact the photosensitive member 1 to charge the photosensitive member. (This mode may be referred to as a "contact charging" mode.) In the apparatus shown in FIGS. 3 and 4, a toner image on the photosensitive member 1 is also transferred onto a recording material 9 by the action of a contact charging member 23. More specifically, the contact charging member 23 supplied with a voltage is caused to contact the recording material 9 to transfer the toner image on the photosensitive member 1 onto the recording material 9.

Further, in the apparatus shown in FIG. 4, at least the photosensitive member 1 and the contact charging member 10 are housed within a first container 21 to form a first process cartridge, and at least a developing means 4 is housed within a second container 22 to form a second process cartridge, so that the first and second process cartridges are detachably mountable to a main assembly of the apparatus. A cleaning means 6 can be disposed or not disposed within the container 21.

In case where the electrophotographic apparatus is used as a copying machine or a printer, exposure light image L may be given as reflected light from or transmitted light through an original, or by converting data read from the original into a signal and effecting a scanning by a semiconductor laser beam, etc., based on the signal.

The electrophotographic photosensitive member according to the present invention is applicable to a semiconductor laser having a short oscillation wavelength of 380–500 nm, preferably 400–450 nm.

Incidentally, the porphyrinato-zinc compounds having a novel crystal form exhibit an excellent function as a photoconductor and are applicable to not only an electrophotographic photosensitive member as mentioned above but also solar cells, sensors, switching devices, etc.

Hereinbelow, the present invention will be described more specifically based on Examples, to which the scope of the present invention should not be construed to be restricted. In the following description, "part(s)" used for describing a relative amount is by weight.

The X-ray diffraction data referred to herein for determining the crystal form of related compounds are based on data measured by X-ray diffractometry using $CuK_\alpha$characteristic X-rays according to the following conditions:

Apparatus: Full-automatic X-ray diffraction apparatus ("MXP18", available from MAC Science K.K.)

| | |
|---|---|
| X-ray tube (Target): | Cu |
| Tube voltage: | 50 kV |
| Tube current: | 300 mA |
| Scanning method: | 2θ/θ scan |
| Scanning speed: | 2 deg./min. |
| Sampling interval: | 0.020 deg. |
| Starting angle (2θ): | 5 deg. |
| Stopping angle (2θ): | 40 deg. |
| Divergence slit: | 0.5 deg. |
| Scattering slit: | 0.5 deg. |
| Receiving slit: | 0.3 mm |
| Curved monochromator: | used. |

Further, IR (infrared spectrometry) data described herein are based on measurement by using "FT/IR-420" (trade name, made by Nippon Bunko K.K.), and elementary analysis data are based on measurement by using "FLASH EA1112" (trade name, made by Thermo Quest Co.).

Various porphyrin compounds were prepared in the following Synthesis Examples 1–11 which were performed with reference to reports of A. Shamin, P. Worthington and P. Hambright, J. Chem. Soc. Pak. 3(1), p. 1–3 (1981); etc.

Synthesis Example 1

To 150 parts of propionic acid placed in a three-necked flask and under refluxing, 4 parts of pyridine-4-aldehyde and 2.8 parts of pyrrole were added dropwise and little by little through two dropping funnels. After the dropwise addition, the system was further subjected to 30 min. of refluxing. The solvent was distilled off under a reduced pressure, and the residue together with a small amount of triethylamine added thereto was purified through a silica gel column with chloroform as the eluent to obtain 1.1 parts of 5,10,15,20-tetra(4-pyridyl)-21H,23H-porphyrin, which exhibited the following elementary analysis and IR data:

| | Measured | Calculated |
|---|---|---|
| C (%) | 75.7 | 77.7 |
| H (%) | 4.5 | 4.2 |
| N (%) | 17.7 | 18.1 |

IR (KBr) peaks: 3467, 1593, 1400, 1068, 970 $cm^{-1}$.

Synthesis Example 2

1 part of 5,10,15,20-tetra(4-pyridyl)-21H,23H-porphyrin and 1 part of zinc chloride were added to 100 parts of N,N-dimethylformamide, and the mixture was subjected to 1 hour of refluxing. After distilling off the solvent under a reduced pressure, the residue was purified through an aluminum column with chloroform as the eluent to obtain 1 part of 5,10,15,20-tetra(4-pyridyl)-21H,23H-porphyrinato-zinc compound, which exhibited the following elementary analysis and IR data:

| | Measured | Calculated |
|---|---|---|
| C (%) | 66.1 | 70.4 |
| H (%) | 4.0 | 3.6 |
| N (%) | 15.6 | 16.4 |

IR (KBr) peaks: 1595, 993 $cm^{-1}$.

Synthesis Example 3

Figure 5:
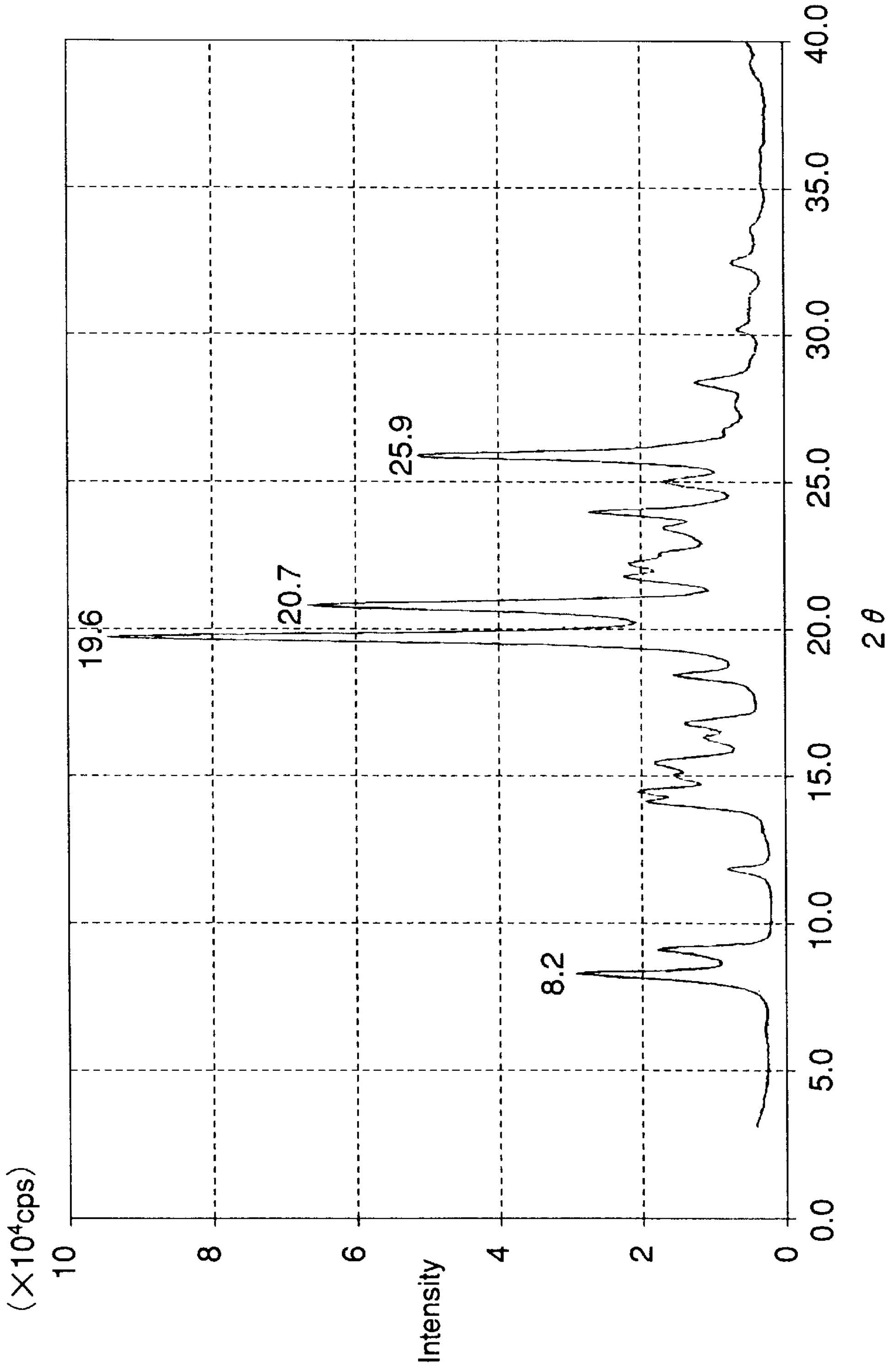
FIGS. 5 to 13 are $CuK_\alpha$-characteristic X-ray diffraction patterns of 5,10,15,20-tetra(4-pyridyl)-21H,23H-porphyrin crystals obtained in Synthesis Examples 3 to 11, respectively.

5 parts of the porphyrin compound obtained in Synthesis Example 1 was dissolved in 150 parts of conc. sulfuric acid at 5° C., and the solution was added dropwise to 750 parts of iced water under stirring to result in a re-crystallizate, which was filtered and subjected to four times of dispersion washing within deionized water, followed by vacuum drying at 40° C. to obtain 3.5 parts of 5,10,15,20-tetra(4-pyridyl)-21H,23H-porphyrin crystal (called Crystal E). Crystal E exhibited the same IR data as the porphyrin compound of Synthesis Example 1 and provided a $CuK_\alpha$-characteristic X-ray diffraction pattern of FIG. 5 showing peaks at Bragg angles (2θ±0.2 deg.) of 8.2 deg., 19.6 deg., 20.7 deg. and 25.9 deg.

Synthesis Example 4

Figure 6:
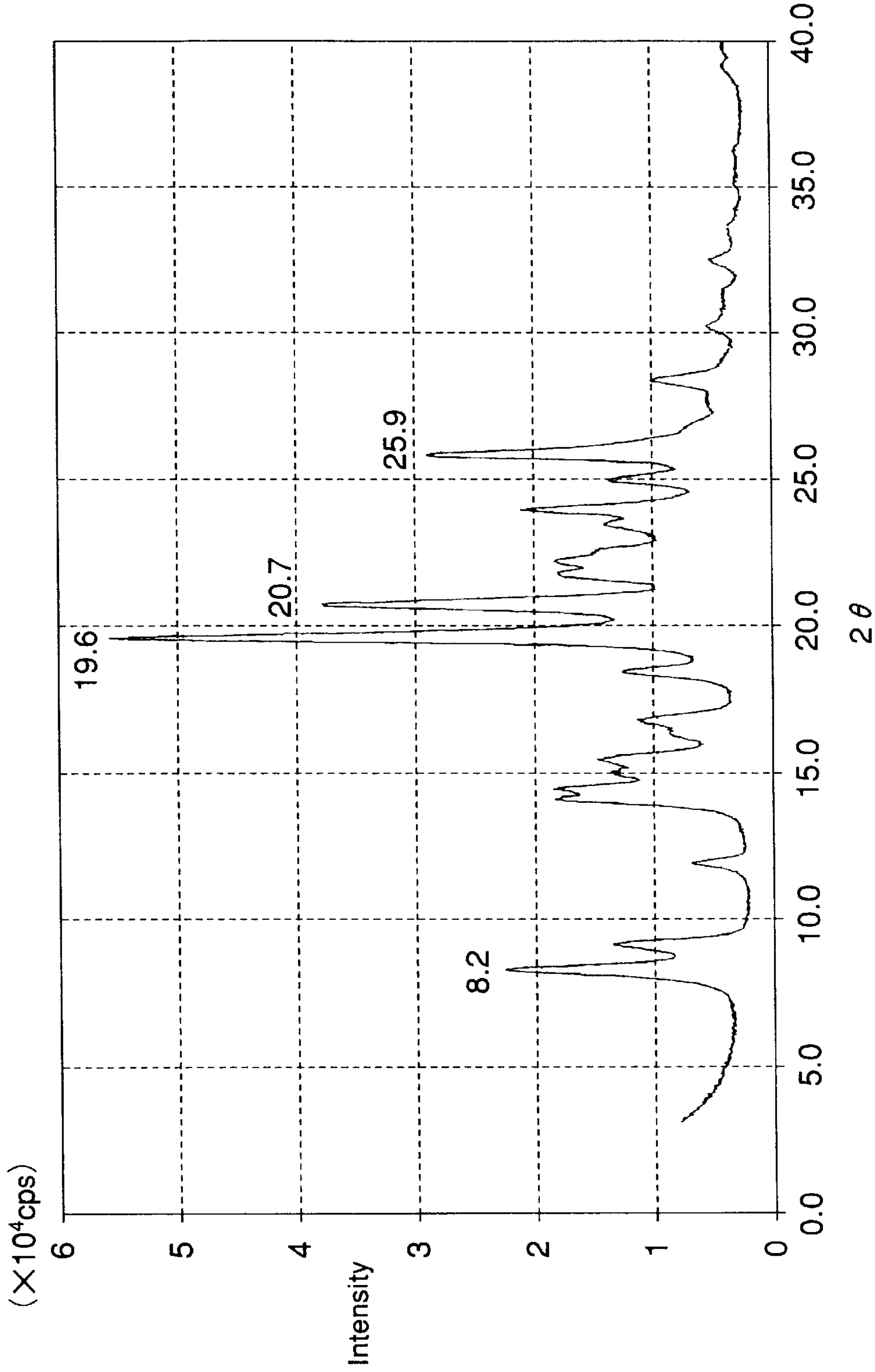

0.5 part of Crystal E obtained in Synthesis Example 3 was subjected to dispersion together with 15 parts of tetrahydrofuran and 15 parts of 1 mm-dia. glass beads for 24 hours in a paint shaker, and then recovered by filtration and dried to obtain a product which was again a type of Crystal E providing a $CuK_\alpha$-characteristic X-ray diffraction pattern of FIG. 6 showing peaks at Bragg angles (2θ±0.2 deg.) of 8.2 deg., 19.6 deg., 20.7 deg. and 25.9 deg.

Synthesis Example 5

Figure 7:
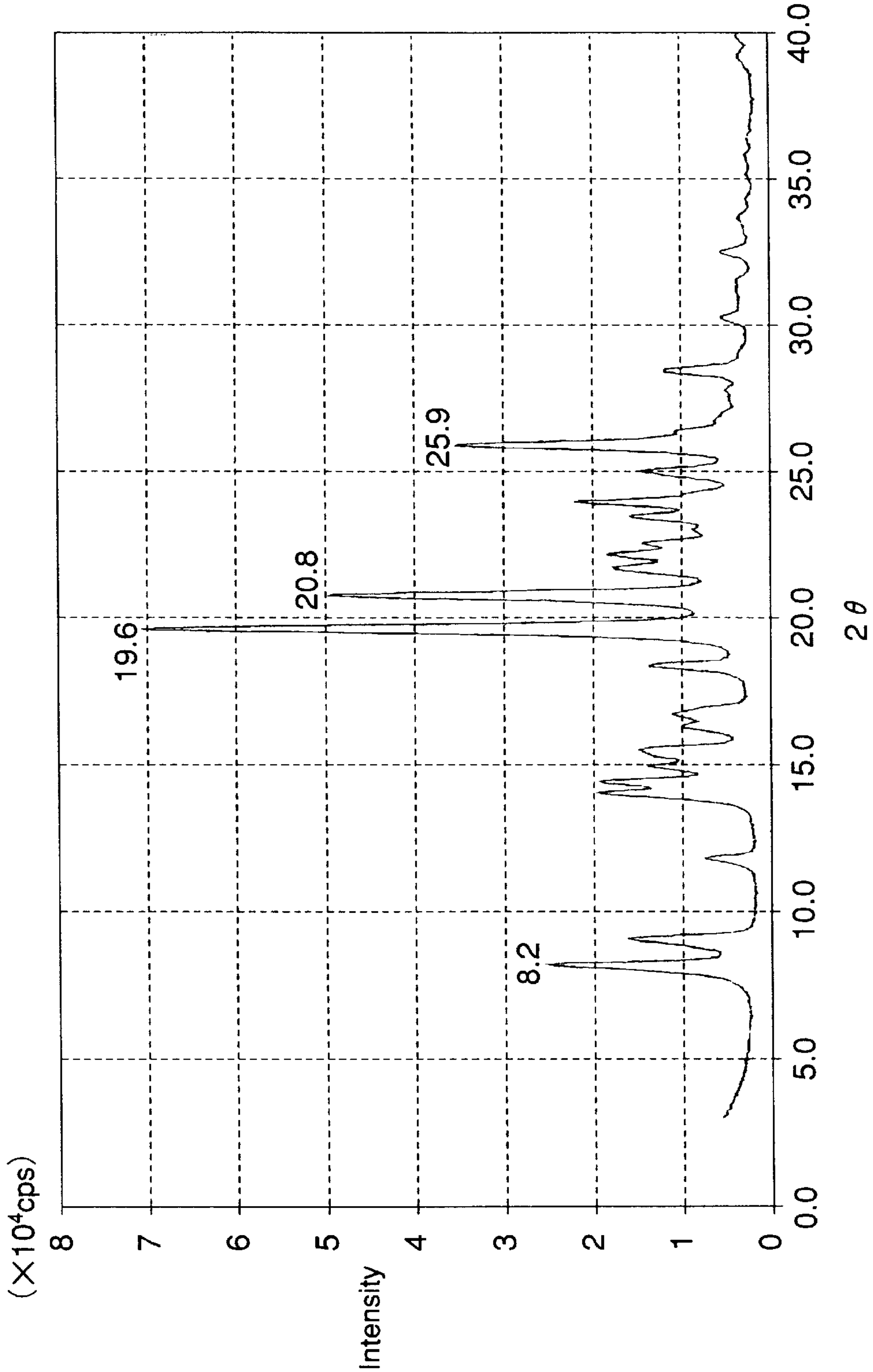

0.5 part of Crystal E obtained in Synthesis Example 3 was subjected to dispersion together with 15 parts of chloroform and 15 parts of 1 mm-dia. glass beads for 24 hours in a paint shaker, and then recovered by filtration and dried to obtain a product which was again a type of Crystal E providing a $CuK_\alpha$-characteristic X-ray diffraction pattern of FIG. 7 showing peaks at Bragg angles (2θ±0.2 deg.) of 8.2 deg., 19.6 deg., 20.7 deg. and 25.9 deg.

Synthesis Example 6

Figure 8:
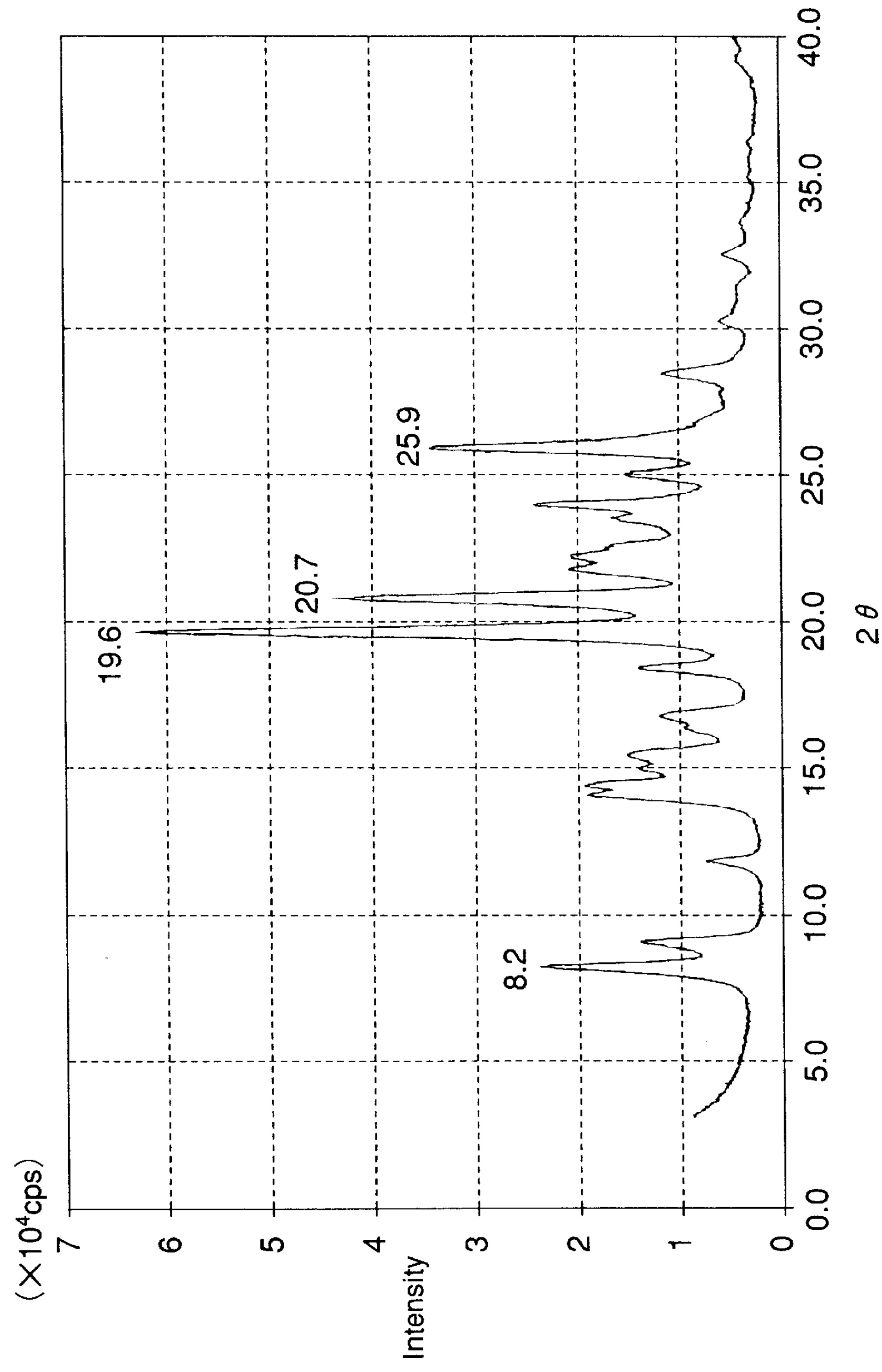
Figure 9:
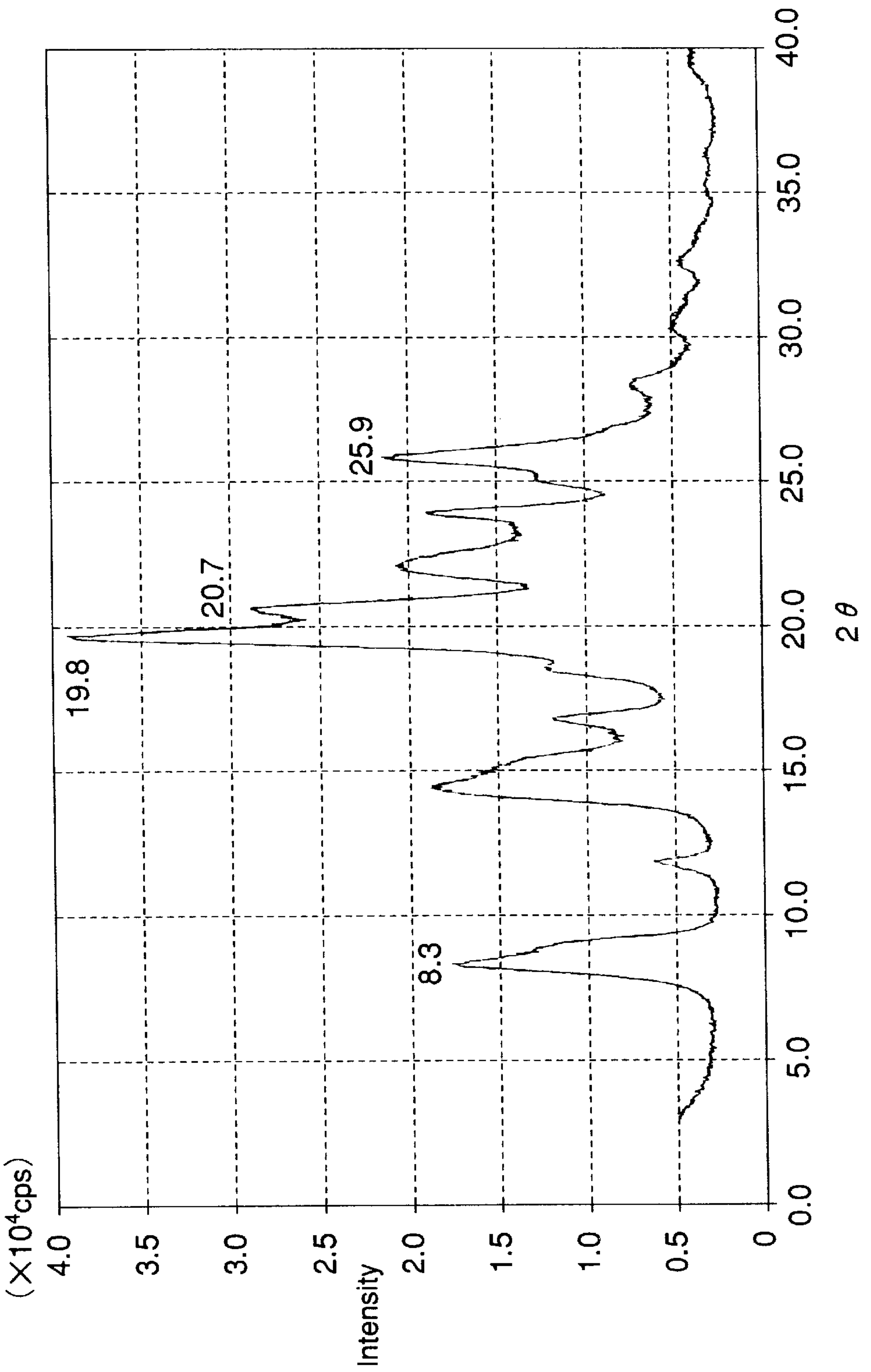

0.5 part of Crystal E obtained in Synthesis Example 3 was subjected to dispersion together with 15 parts of N,N-dimethylformamide and 15 parts of 1 mm-dia. glass beads for 24 hours in a paint shaker, and then recovered by filtration and dried to obtain a product which was again a type of Crystal E providing a $CuK_\alpha$-characteristic X-ray diffraction pattern of FIG. 8 showing peaks at Bragg angles (2θ±0.2 deg.) of 8.2 deg., 19.6 deg., 20.7 deg. and 25.9 deg.

Synthesis Example 7

0.5 part of Crystal E obtained in Synthesis Example 3 was subjected to dispersion together with 15 parts of 1 mm-dia. glass beads for 24 hours in a paint shaker, and then recovered by aqueous ultrasonic treatment (i.e., ultrasonic dispersion in an aqueous medium) and filtration and dried to obtain a product which was again a type of Crystal E providing a $CuK_\alpha$-characteristic X-ray diffraction pattern of FIG. 5 showing peaks at Bragg angles (2θ±0.2 deg.) of 9 deg., 19.8 deg., 20.7 deg. and 25.9 deg.

Synthesis Example 8

Figure 10:
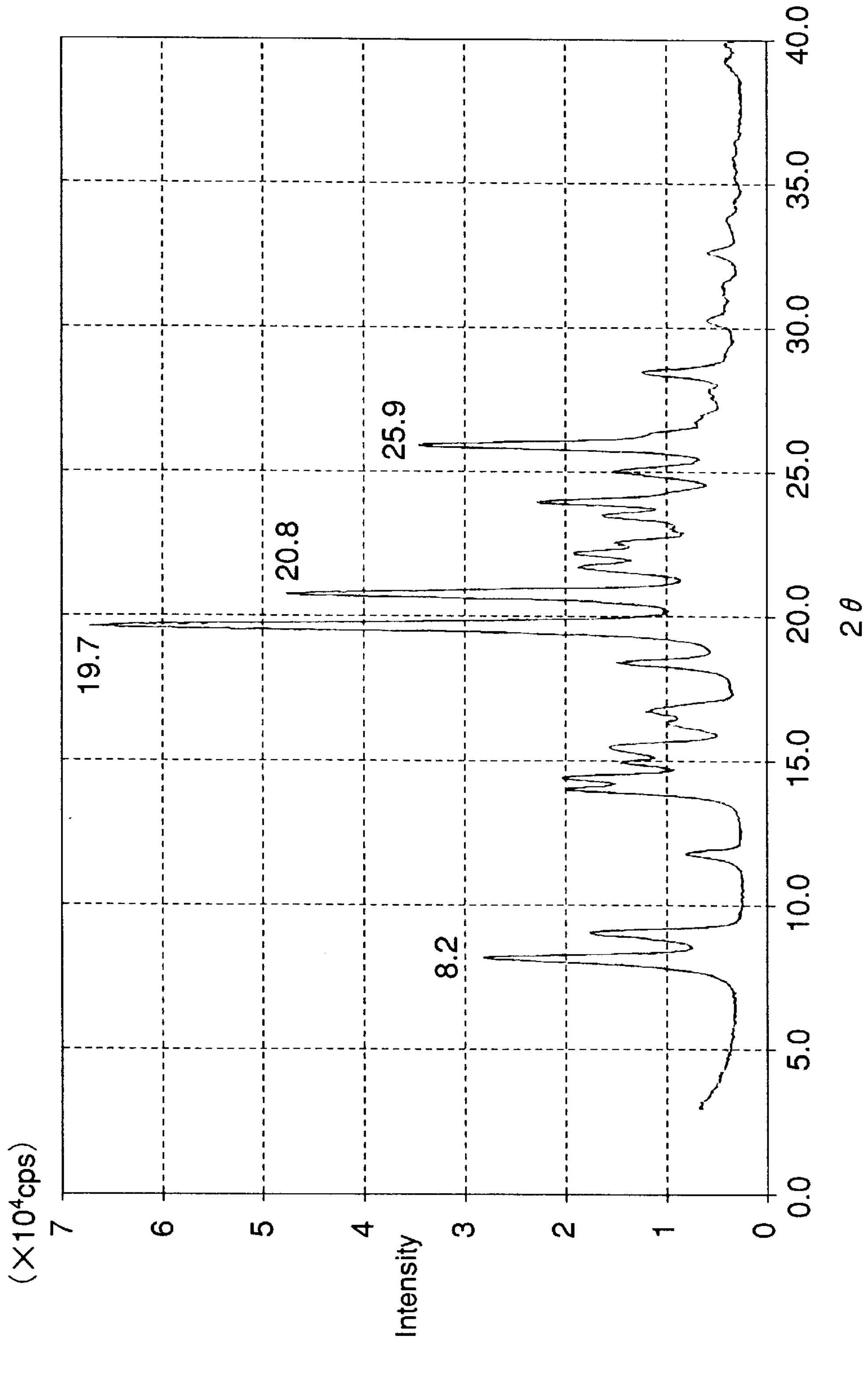

0.5 part of Crystal E obtained in Synthesis Example 3 was subjected to dispersion together with 15 parts of methanol and 15 parts of 1 mm-dia. glass beads for 24 hours in a paint shaker, and then recovered by filtration and dried to obtain a product which was again a type of Crystal E providing a $CuK_\alpha$-characteristic X-ray diffraction pattern of FIG. 10 showing peaks at Bragg angles (2θ±0.2 deg.) of 8.2 deg., 19.7 deg., 20.8 deg. and 25.9 deg.

Synthesis Example 9

Figure 11:
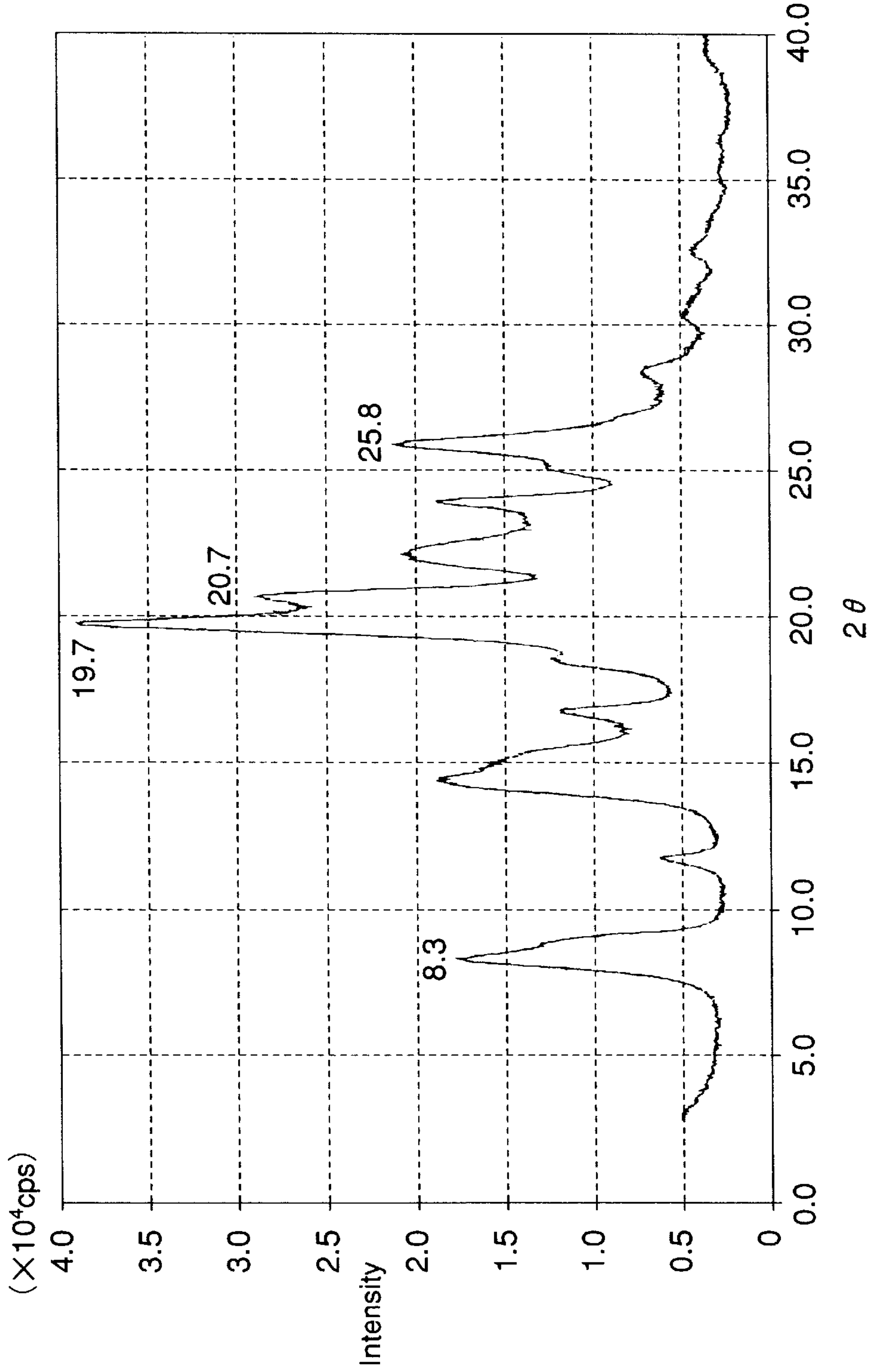

0.5 part of Crystal E obtained in Synthesis Example 6 was subjected to dispersion together with 15 parts of 1 mm-dia. glass beads for 24 hours in a paint shaker, and then recovered by aqueous ultrasonic treatment and filtration and dried to obtain a product which was again a type of Crystal E providing a $CuK_\alpha$-characteristic X-ray diffraction pattern of FIG. 11 showing peaks at Bragg angles (2θ±0.2 deg.) of 8.3 deg., 19.7 deg., 20.7 deg. and 25.8 deg.

Synthesis Example 10

Figure 12:
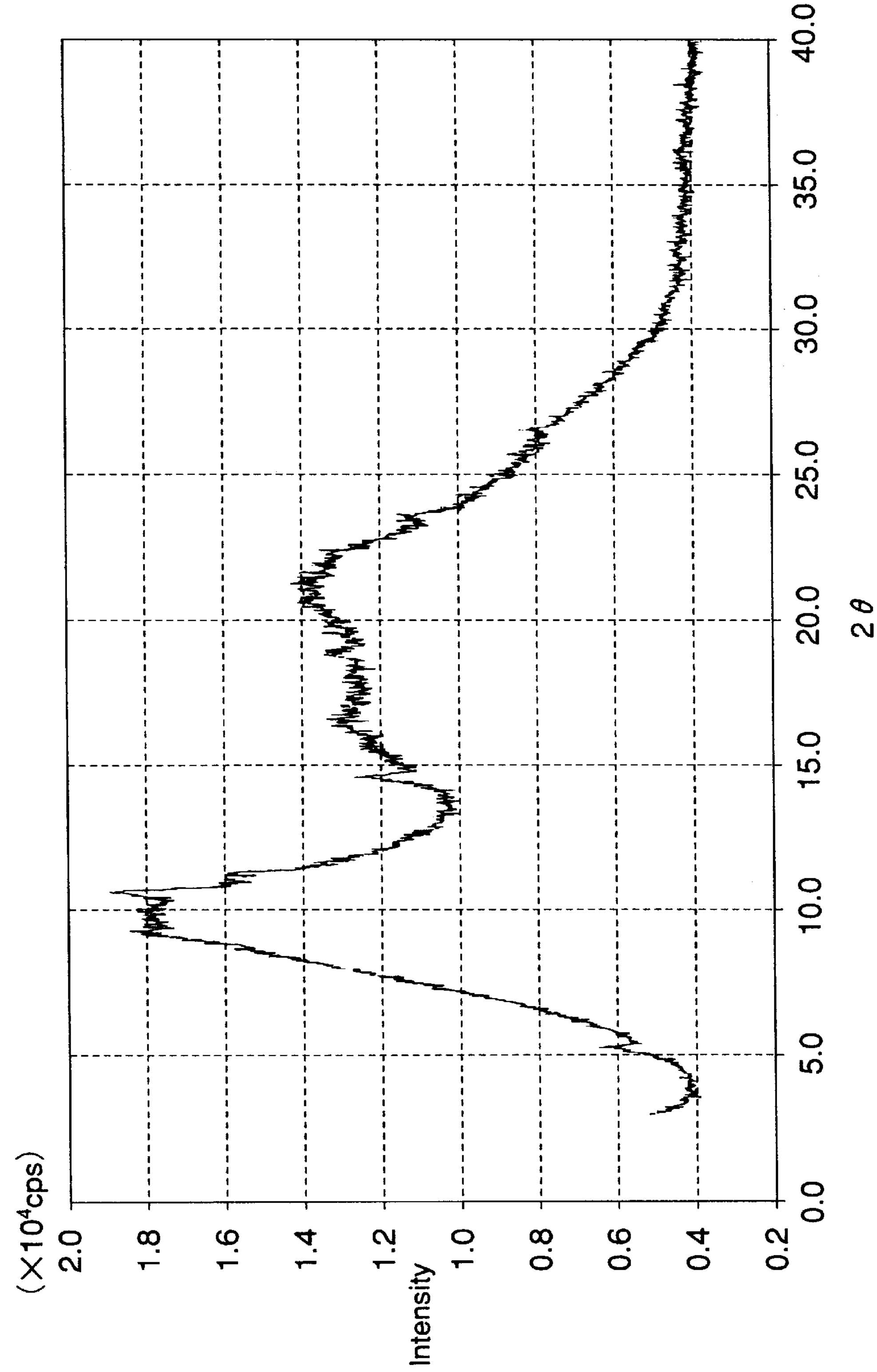

0.5 part of porphyrinato-zinc compound obtained in Synthesis Example 2 was subjected to dispersion together with 15 parts of 1 mm-dia. glass beads for 24 hours in a paint shaker, and then recovered by aqueous ultrasonic treatment and filtration and dried to obtain an amorphous 5,10,15,20-tetra(4-pyridyl)-21H,23H porphyrinato-zinc compound providing a $CuK_\alpha$-characteristic X-ray diffraction pattern of FIG. 12 showing no clear peaks.

Synthesis Example 11

Figure 13:
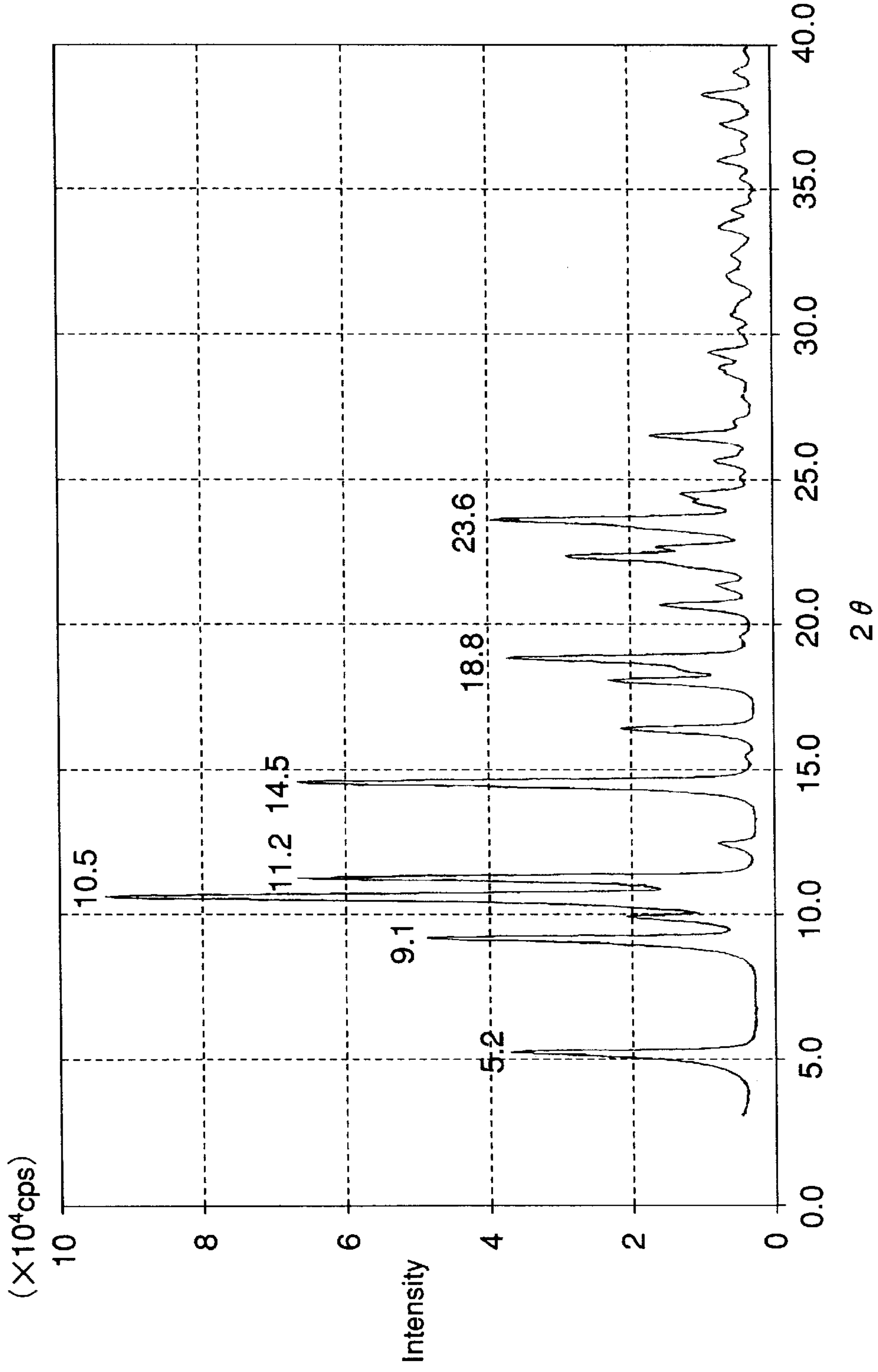

0.5 part of the porphyrinato-zinc compound obtained in Synthesis Example 10 was subjected to dispersion together with 15 parts of tetrahydrofuran and 15 parts of 1 mm-dia. glass beads for 24 hours in a paint shaker, and then recovered by filtration and dried to obtain a product which was a type of Crystal D providing a $CuK_\alpha$-characteristic X-ray diffraction pattern of FIG. 13 showing peaks at Bragg angles (2θ±0.2 deg.) of 9.1 deg., 10.5 deg., 11.2 deg. and 14.5 deg.

Example 1-1

Figure 14:
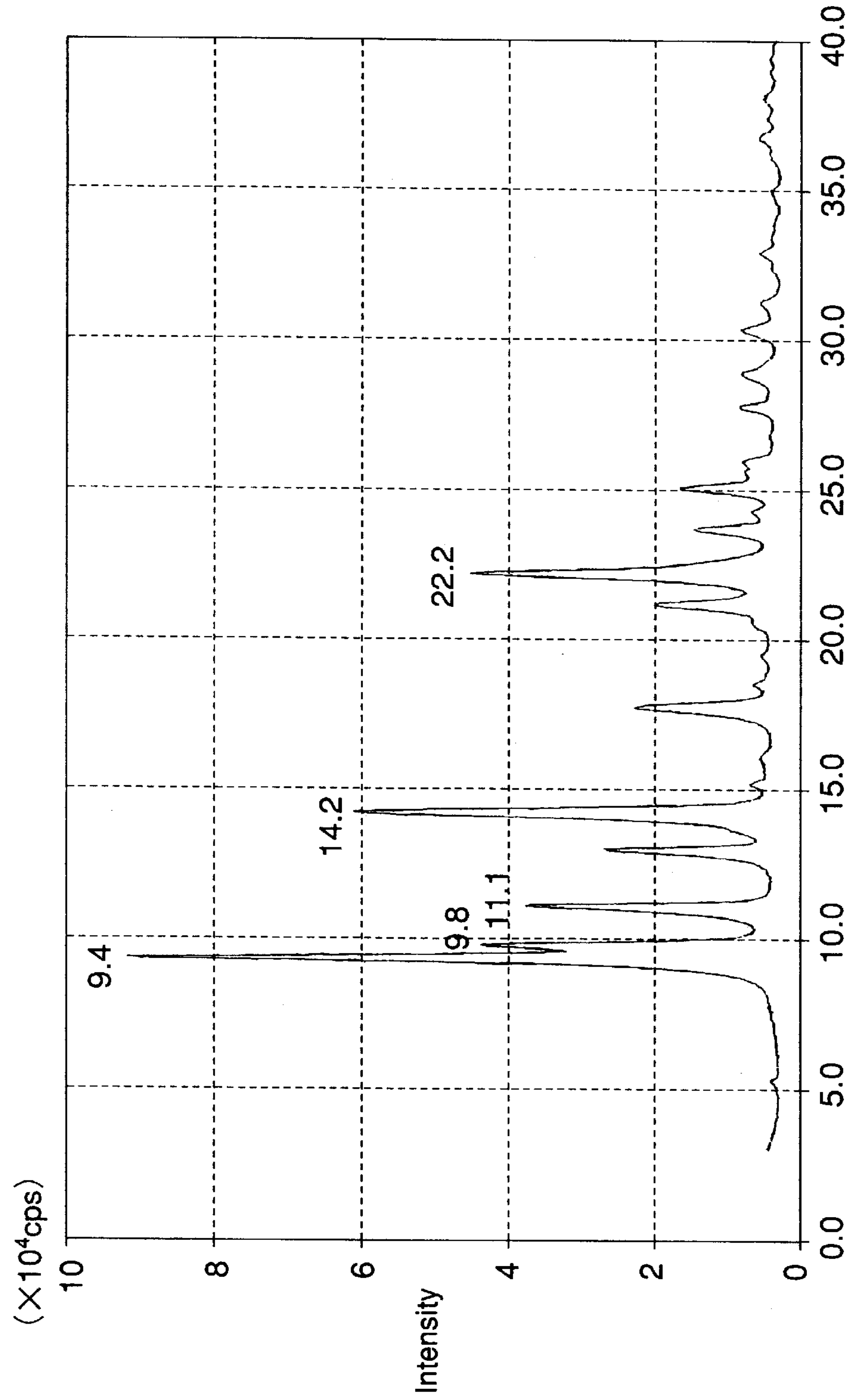
FIGS. 14 to 16 are $CuK_\alpha$-characteristic X-ray diffraction patterns of 5,10,15,20-tetra(4-pyridyl)-21H,23H-porphyrin crystals obtain in Examples 1-1 to 1-3, respectively.

0.5 part of the porphyrinato-zinc compound obtained in Synthesis Example 10 was subjected to dispersion together with 15 parts of chloroform and 15 parts of 1 mm-dia. glass beads for 24 hours in a paint shaker, and then recovered by filtration and dried to obtain a product which was a type of Crystal A providing a $CuK_\alpha$-characteristic X-ray diffraction pattern of FIG. 14 showing peaks at Bragg angles (2θ±0.2 deg.) of 9.4 deg., 14.2 deg. and 22.2 deg.

Example 1-2

Figure 15:
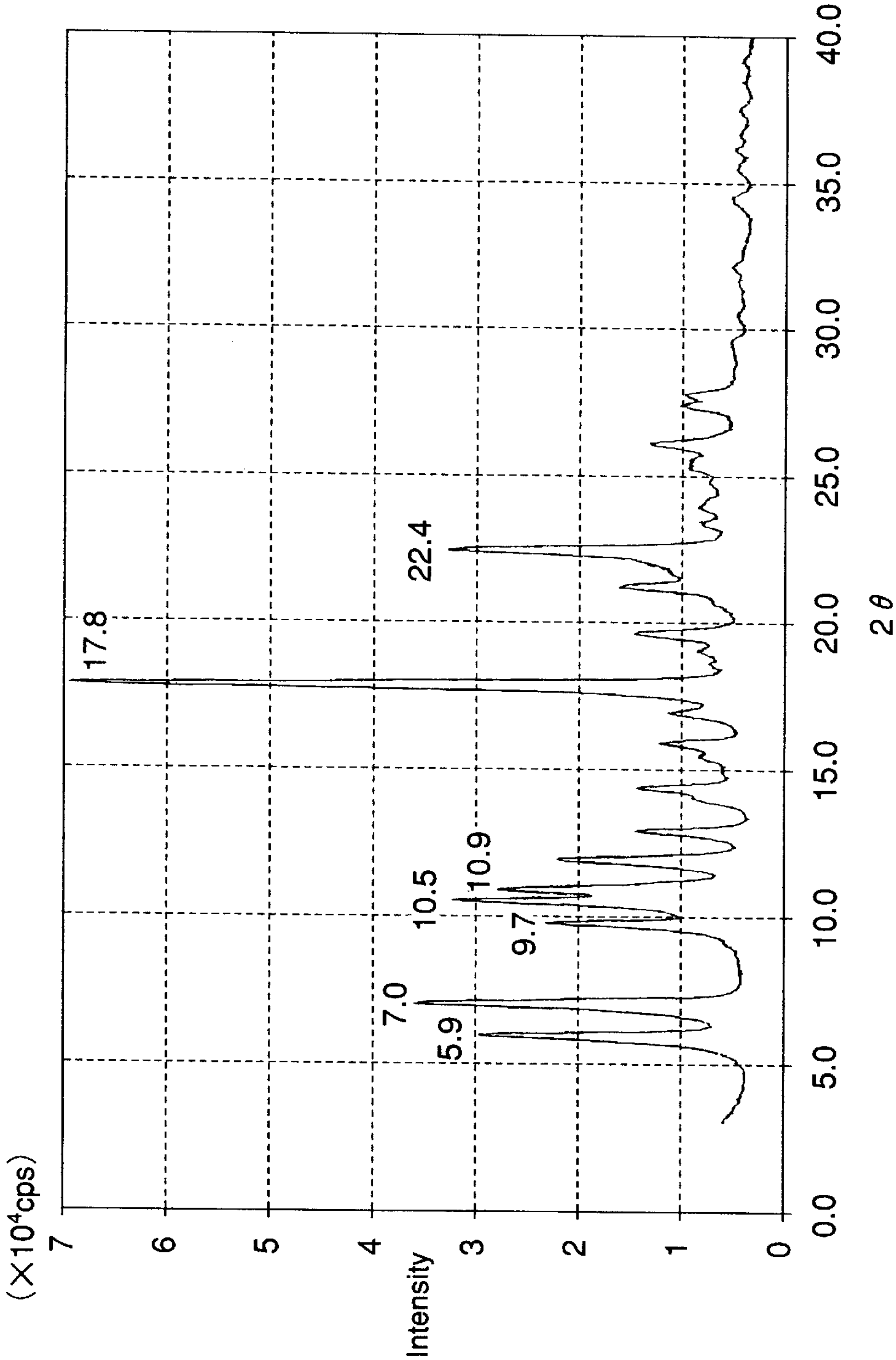

0.5 part of the porphyrinato-zinc compound obtained in Synthesis Example 10 was subjected to dispersion together with 15 parts of N,N-dimethylformamide and 15 parts of 1 mm-dia. glass beads for 24 hours in a paint shaker, and then recovered by filtration and dried to obtain a product which was a type of Crystal B providing a $CuK_\alpha$-characteristic X-ray diffraction pattern of FIG. 15 showing peaks at Bragg angles (2θ±0.2 deg.) of 7.0 deg., 10.5 deg., 17.8 deg. and 22.4 deg.

Example 1-3

Figure 16:
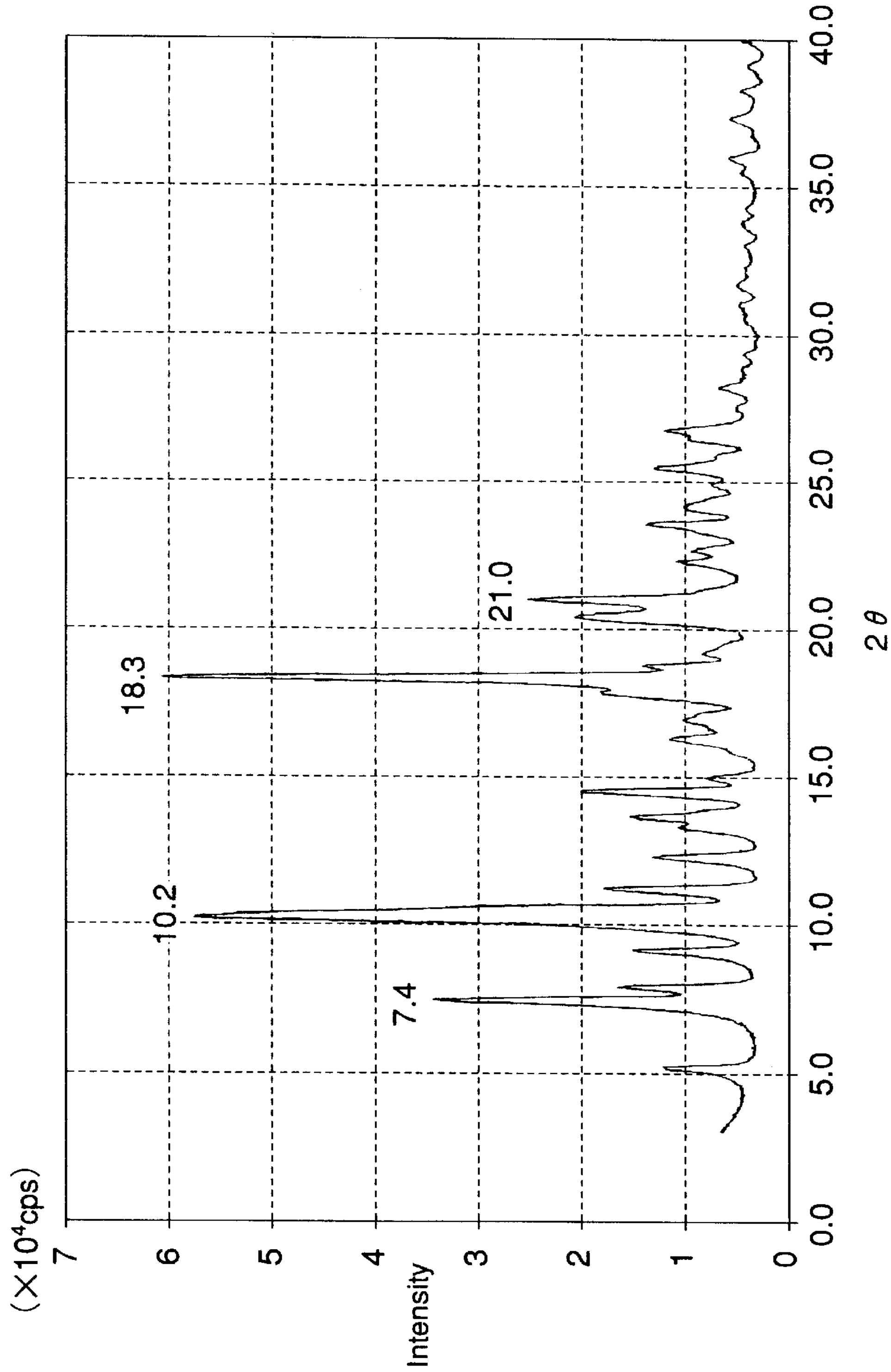

0.5 part of the porphyrinato-zinc compound obtained in Synthesis Example 10 was subjected to dispersion together with 15 parts of methanol and 15 parts of 1 mm-dia. glass beads for 24 hours in a paint shaker, and then recovered by filtration and dried to obtain a product which was a type of Crystal C providing a $CuK_\alpha$-characteristic X-ray diffraction pattern of FIG. 16 showing peaks at Bragg angles (2θ±0.2 deg.) of 7.4 deg., 10.2 deg. and 18.3 deg.

Example 2-1

5 parts of methoxymethylated nylon (Mav (average molecular weight)=32000) and 10 parts of alcohol-soluble copolymer nylon (Mav =29000) were dissolved in 95 parts of methanol to obtain a coating liquid, which was applied by means of a wire bar onto an aluminum sheet of 15 cm×20 cm and dried to form a 0.5 μm-thick undercoating layer.

Then, 4 parts of Crystal E (5,10,15,20-tetra(4-pyridyl)-21H,23H-porphyrinato-zinc crystal) obtained in Synthesis Example 3 was added to a solution of 2 parts of polyvinylbutyral resin ("BX-1", made by Sekisui Kagaku Kogyo K.K.) in 100 parts of cyclohexanone, and the mixture was subjected to 3 hours of dispersion in a paint shaker, followed by dilution with 150 parts of ethyl acetate, to obtain a dispersion liquid, which was then applied by a wire bar over the undercoating layer and dried to form a 0.2 μm-thick charge generation layer.

Then, 5 parts of triphenyl compound represented by a formula shown below:

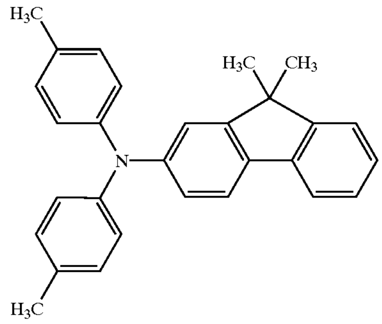

and 5 parts of polycarbonate resin ("IUPILON Z200", made by Mitsubishi Engineering-Plastics K.K.), were dissolved in 35 parts of chlorobenzene to obtain a coating liquid, which was applied by a wire bar over the charge generation layer and dried to form a 20 μm-thick charge transport layer, thereby obtaining an electrophotographic photosensitive member.

Examples 2-2 to 2-12

Eleven photosensitive members were prepared in the same manner as in Example 2-1 except for using porphyrin compounds or crystals prepared in Examples or Synthesis Examples shown in Table 1 appearing hereinafter as the charge-generating material instead of Crystal E.

Comparative Example 2-1

A photosensitive member was prepared in the same manner as in Example 2-1, except for using Comparative Azo Compound A having a structure shown below:

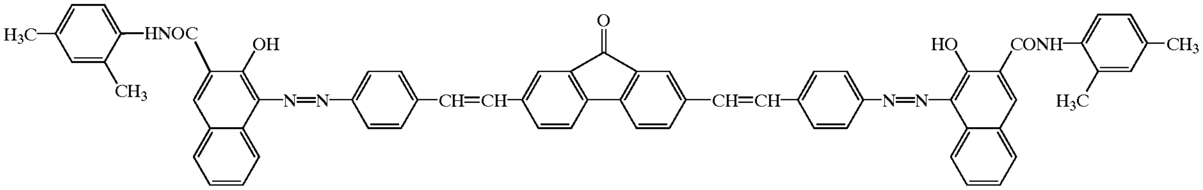

Comparative Example 2-2

Figure 17:
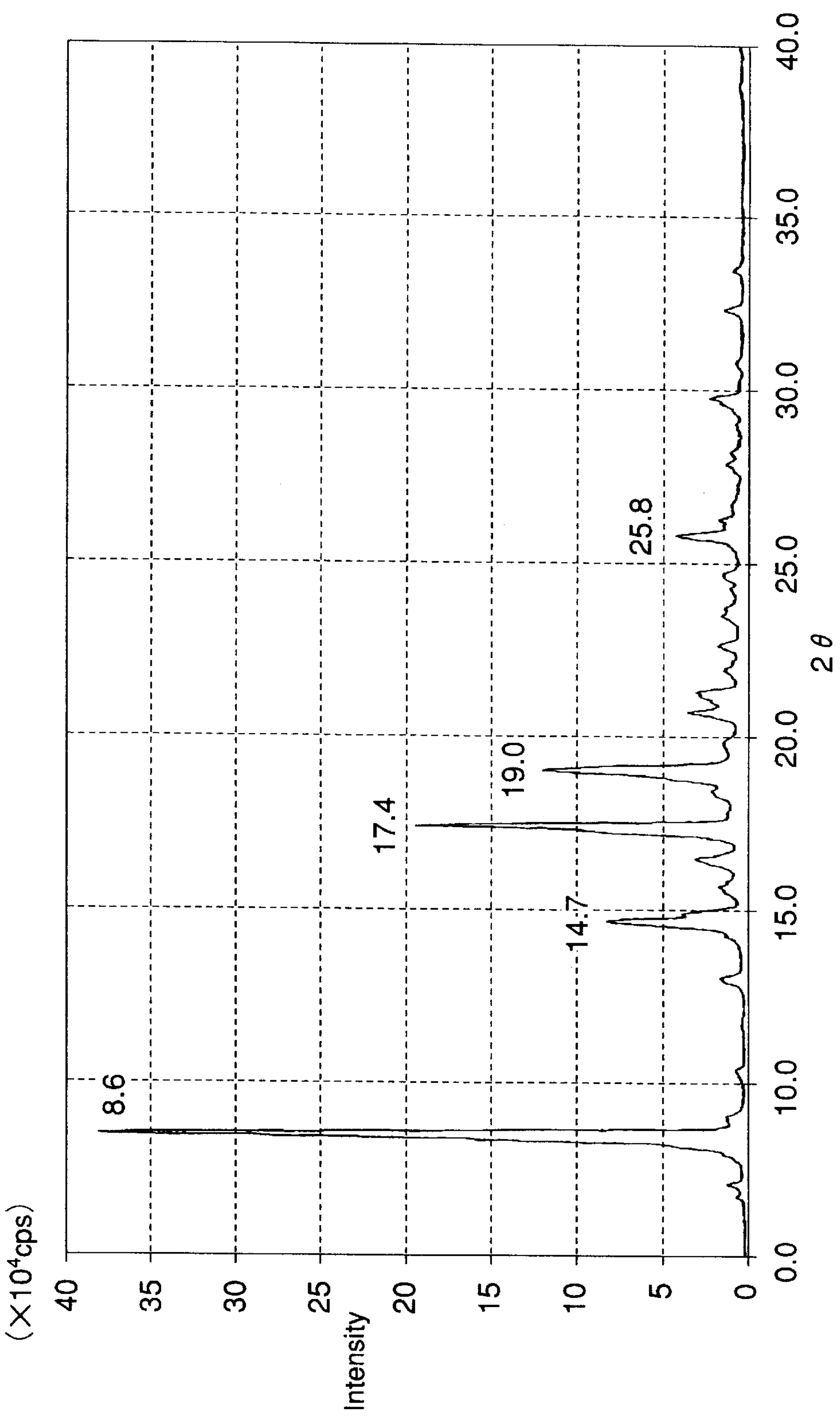
FIG. 17 is a $CuK_\alpha$-characteristic X-ray diffraction pattern of 5,10,15,20-tetraphenyl-21H,23H-porphyrin crystal used in Comparative Example 2.

A photosensitive member was prepared in the same manner as in Example 2-1 except for using Comparative Porphyrin Compound B having a structure shown below (i.e., 5,10,15,20-tetraphenyl-21H,23H-porphyrin) obtained in the same manner as in Synthesis Example 1 except for using benzaldehyde instead of the pyridine-4-aldehyde and giving a $CuK_\alpha$-characteristic X-ray diffraction pattern of FIG. 17 showing peaks at Bragg angles (2θ±0.2 deg.) of 8.6 deg., 14.7 deg., 17.4 deg. as the charge-generating material instead of Crystal E.

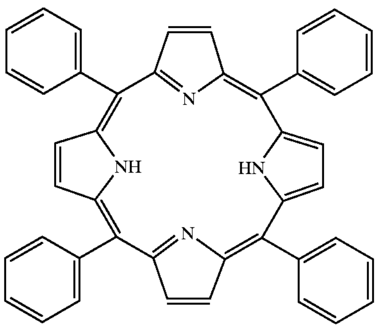

Sensitivity Test

Each of the photosensitive members prepared in above Examples and Comparative Examples were subjected a sensitivity test as follows.

For the test, each photosensitive member was charged to an initial surface potential of −700 volts and exposed to monochromatic light having a wavelength of 403 nm obtained by passing light from a halogen lamp through an interference filter and transmitted through an electroconductive NESA glass sheet of 10 $cm^2$ (for imparting the surface potential to the photosensitive member and measuring a surface potential after exposure of the photosensitive member) disposed in contact with the photosensitive member, thereby measuring a half-attenuation exposure energy $E_{1/2}$ ($\mu J/cm^2$) required for lowering the surface potential to a half (−350 volts).

The results of the measurements are inclusively shown in Table 1 below.

TABLE 1

| Example | Porphyrin compound Example | Porphyrin compound Crystal | Half-attenuation energy $E_{1/2}$ at 403 nm [$\mu J/cm^2$] |
|---|---|---|---|
| 2-1 | Synthesis 3 | E | 2.36 |
| 2-2 | Synthesis 4 | E | 1.27 |
| 2-3 | Synthesis 5 | E | 1.69 |
| 2-4 | Synthesis 6 | E | 1.19 |
| 2-5 | Synthesis 7 | E | 0.86 |
| 2-6 | Synthesis 8 | E | 1.23 |
| 2-7 | Synthesis 9 | E | 1.01 |
| 2-8 | Synthesis 10 | amorphous | 4.78 |
| 2-9 | Synthesis 11 | D | 14.9 |
| 2-10 | 1-1 | A | 6.23 |
| 2-11 | 1-2 | B | 8.52 |
| 2-12 | 1-3 | C | 8.59 |
| Comp. 2-1 | Comp. A Compd. *1 | — | 94 |
| Comp. | Comp. B Compd. *2 | — | *3 |

*1: Azo compound.
*2: Metal-free tetraphenyl-porphyrin compound.
*3: The measurement of $E_{1/2}$ was impossible because substantially no surface potetial lowering was caused by the exposure.

Example 3-1

An electroconductive paint was prepared by subjecting a mixture of 50 parts of titanium oxide powder coated with 10%-antimony oxide-containing tin oxide, 25 parts of resol-type phenolic resin, 20 parts of methyl cellosolve, 5 parts of methanol and 0.002 part of silicone oil (polydimethylsiloxane-polyoxyalkylene copolymer, Mav=3000) to 2 hours of dispersion together with 1.2 mm-dia. glass beads in a sand mill.

A 62 mm-dia. aluminum cylinder was coated with the above-prepared electroconductive paint by dipping and dried for 30 min. at 140° C. to form a 16 $\mu$m-thick electroconductive layer.

A solution of 5 parts of 6-66-61-12 quaternary polyamide copolymer resin in a mixture solvent of 70 parts of methanol and 25 parts of butanol was applied by dipping on the electroconductive layer, and dried to form a 0.6 $\mu$m-thick undercoating layer.

Then, 2.5 parts of Crystal E prepared in Synthesis Example 7 and 1 part of polyvinylbutyral resin ("ESLEC BX-1", made by Sekisui Kagaku Kogyo K.K.) were added to 50 parts of cyclohexanone, and the mixture was dispersed for 6 hours together with 1.2 mm-dia. glass beads in a sand mill, followed by dilution with 40 parts of cyclohexanone and 60 parts of ethyl acetate to obtain a paint, which was then applied by dipping onto the undercoating layer and dried for 20 min. at 130° C. to form a 0.20 $\mu$m-thick charge generation layer.

Then, 8 parts of the triphenylamine compound used in Example 2-1 and 1 part a triphenylamine compound represented by a formula shown below:

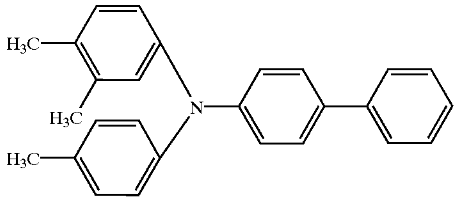

were dissolved together with polycarbonate resin ("IUPILON Z400", made by Mitsubishi Engineering-Plastics K.K.) in a mixture solvent of 70 parts of monochlorobenzene and 30 parts of methylal to form a paint, which was applied by dipping on the charge generation layer and dried for 1 hour at 110° C. to form a 17 μm-thick charge transport layer, thereby obtaining an electrophotographic photosensitive member.

The thus-prepared photosensitive member was incorporated in a commercially available laser beam printer ("COLOR LASER SHOT-LBP 2360", made by Canon K.K.) after remodeling of replacing the laser unit with a violet, semiconductor laser having an oscillation wavelength of 405 nm ("VIOLET LASER DIODE", made by Nichia Kagaku Kogyo K.K.) together with an associated optical system, and subjected to image formation. As a result, images having a high resolution and good gradation characteristic were obtained.

As described above, according to the present invention, a porphyrin compound having a specific structure is incorporated in a photosensitive layer to provide an electrophotographic photosensitive member which can exhibit an excellent sensitivity when used in combination with an exposure system including a semiconductor laser having a short oscillation wavelength of 380–500 nm. There are further provided a process-cartridge and an electrophotographic apparatus including such a photosensitive member.

What is claimed is:

1. A 5,10,15,20-tetrapyridyl-21H,23Hporphyrinato-zinc compound having a crystal form selected from the group consisting of (a), (b) and (c) shown below:

(a) a crystal form characterized by peaks at Bragg angles (2θ±0.2 deg.) of 9.4 deg., 14.2 deg. and 22.2 deg., (b) a crystal form characterized by peaks at Bragg angles (2θ±0.2 deg.) of 7.0 deg., 10.5 deg. and 22.4 deg., and (c) a crystal form characterized by peaks at Bragg angles (2θ+0.2 deg.) of 7.4 deg., 10.2 deg and 18.3 deg., respectively in CuKα-characteristic X-ray diffraction patterns.

2. A 5,10,15-20-tetrapyridyl-21H,23H-porphyrinato-zinc compound having the crystal form (a).

3. A 5,10,15-20-tetrapyridyl-21H,23H-porphyrinato-zinc compound according to claim 1 having the crystal form (b).

4. A 5,10,15-20-tetrapyridyl-21H,23H-porphyrinato-zinc compound according to claim 1 having the crystal form (c).

* * * * *

UNITED STATES PATENT AND TRADEMARK OFFICE

CERTIFICATE OF CORRECTION

PATENT NO. : 6,683,175 B2
APPLICATION NO. : 10/119003
DATED : January 27, 2004
INVENTOR(S) : Masato Tanaka It is certified that error appears in the above-identified patent and that said Letters Patent is hereby corrected as shown below:

<u>COVER PAGE [56] References Cited</u>

FOREIGN PATENT DOCUMENTS

"05275771" should read --5-275771--; and
"06136278" should read --6-136278--.

<u>Column 10</u>

Line 56, "0.1-μm" should read --0.1-10 μm--.

<u>Column 11</u>

Line 27, "5-30 μm" should read --5-40 μm--; and
Line 28, "10-30 μm. The" should read --10-30 μm. ¶The--.

<u>Column 20</u>

Line 10, "23Hporphyrinato-" should read --23H-porphyrinato---;
Line 19, "(2θ+0.2" should read --(2θ±0.2--;
Line 20, "CuKα-characteristic" should read --$CuK_{\alpha}$-characteristic--; and
Line 23, "compound" should read --compound according to claim 1--.

Signed and Sealed this

Twenty-ninth Day of August, 2006

JON W. DUDAS
*Director of the United States Patent and Trademark Office*